US012109455B2

(12) United States Patent
Thatha

(10) Patent No.: US 12,109,455 B2
(45) Date of Patent: Oct. 8, 2024

(54) DATA-DRIVEN ASSISTANCE FOR USERS INVOLVED IN PHYSICAL ACTIVITIES

(71) Applicant: SONY GROUP CORPORATION, Tokyo (JP)

(72) Inventor: Sri Ranganadh Thatha, Bangalore (IN)

(73) Assignee: SONY GROUP CORPORATION, Tokyo (JP)

( * ) Notice: Subject to any disclaimer, the term of this patent is extended or adjusted under 35 U.S.C. 154(b) by 439 days.

(21) Appl. No.: 17/391,789

(22) Filed: Aug. 2, 2021

(65) Prior Publication Data
US 2023/0034143 A1 Feb. 2, 2023

(51) Int. Cl.
*A63B 24/00* (2006.01)
*A63B 71/06* (2006.01)
(Continued)

(52) U.S. Cl.
CPC ...... *A63B 24/0062* (2013.01); *A63B 24/0075* (2013.01); *A63B 71/0622* (2013.01); *G01P 13/00* (2013.01); *G01P 15/18* (2013.01); *G06N 20/20* (2019.01); *A63B 2024/0068* (2013.01); *A63B 2071/0647* (2013.01);
(Continued)

(58) Field of Classification Search
CPC ............ A63B 24/0062; A63B 24/0075; A63B 71/0622; A63B 2024/0068; A63B 2071/0647; A63B 2071/065; A63B 2230/42; A63B 2230/62; G01P 13/00; G01P 15/18; G06N 20/20; A61B 5/1112; A61B 5/1114; G16H 20/30
See application file for complete search history.

(56) References Cited

U.S. PATENT DOCUMENTS 9,248,340 B2 * 2/2016 Hoffman .......... H04M 1/724094
2014/0357960 A1 12/2014 Phillips et al.
(Continued)

FOREIGN PATENT DOCUMENTS

WO WO-2020259858 A1 * 12/2020 ......... A63B 69/3608

OTHER PUBLICATIONS

Valsted, et al., "Strive: exploring assistive haptic feedback on the run", Proceedings of the 29th Australian Conference on Computer-Human Interaction, Brisbane, Australia, Nov. 2017, pp. 275-284.

*Primary Examiner* — Francis C Gray
(74) *Attorney, Agent, or Firm* — CHIP LAW GROUP

(57) ABSTRACT

An electronic device and method for data-driven assistance for users involved in physical activities is provided. The electronic device receives first sensor data associated with a movement pattern of one or more parts of a body of a user and receives first information associated with a location where the user performs the physical activity. The electronic device determines one or more first indicators which are likely to have affected the user or the performance of the user in the physical activity. Thereafter, the electronic device generates presentation data based on an application of a first machine learning model on the determined one or more first indicators and the received first information. The generated presentation data includes one or more improvement suggestions for the user in relation to the physical activity. The electronic device controls a display device to display the presentation data.

18 Claims, 19 Drawing Sheets

(51) Int. Cl.
   *G01P 13/00* (2006.01)
   *G01P 15/18* (2013.01)
   *G06N 20/20* (2019.01)

(52) U.S. Cl.
   CPC ..... *A63B 2071/065* (2013.01); *A63B 2230/42* (2013.01); *A63B 2230/62* (2013.01)

(56) References Cited

U.S. PATENT DOCUMENTS

| | | |
|---|---|---|
| 2019/0183430 A1 | 6/2019 | Alphonse |
| 2019/0366154 A1 | 12/2019 | Callaghan |
| 2021/0008413 A1* | 1/2021 | Asikainen ............. G06F 3/0304 |
| 2021/0100628 A1* | 4/2021 | Posnack ................ G16H 20/30 |

* cited by examiner

DATA-DRIVEN ASSISTANCE FOR USERS INVOLVED IN PHYSICAL ACTIVITIES

CROSS-REFERENCE TO RELATED APPLICATIONS/INCORPORATION BY REFERENCE

None.

FIELD

Various embodiments of the disclosure relate to data analytics, signal processing, and machine learning. More specifically, various embodiments of the disclosure relate to an electronic device and method for data-driven assistance for users involved in physical activities.

BACKGROUND

Advancements in data analytics, signal processing, and machine learning have provided ways to assist people in performing various activities. In sports, an athlete may face an injury while performing or training for a physical activity. For example, while practicing for running, an athlete may face any of the various knee injuries. In some instances, these injuries may happen due to an improper co-ordination between various body parts while the athlete performs or trains for the physical activity. Without any corrective measure, the athlete's performance may degrade over time as a result of such improper coordination or injuries.

Limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic device and a method for data-driven assistance for users involved in physical activities is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

The following described implementations may be found in the disclosed electronic device and method for data-driven assistance for users involved in physical activities. Such an assistance may be useful for athletes to avoid injuries and enhance their performance in the physical activities. Exemplary aspects of the disclosure provide an electronic device (for example, a server or a wearable electronic device) that may be configured to receive sensor data associated with a movement pattern of one or more parts of a body of a user (such as an athlete). The sensor data may correspond to a duration in which the user performs a physical activity (such as running). The electronic device further receives information associated with a location where the user performs the physical activity. Based on the received sensor data, the electronic device may determine one or more first indicators which may be likely to have affected the user or the performance of the user in the physical activity. Thereafter, the electronic device may generate presentation data based on application of a machine learning model on the determined one or more first indicators and the received information. The generated presentation data may include one or more improvement suggestions for the user in relation to the physical activity. Additionally, the presentation data may include insights about the movement pattern or other factors related to performance of the athlete. The electronic device may control a display device to display the presentation data.

By use of the machine learning model, the disclosed electronic device may be able to provide customized improvement suggestions and insights about the movement pattern or other factors related to performance of the athlete in one or more physical activities. Such suggestions and insights may help the athlete to avoid injuries, correct the movement pattern of body parts, and/or enhance the performance in physical activities. The disclosed electronic device may consider information, such as the environmental and terrain conditions associated with the location where the athlete performs the physical activity to provide customized suggestions. In addition to the suggestions, the disclosed electronic device may be able to classify each athlete as one of an amateur athlete, an average athlete, or an expert athlete and may be able to determine one or more injuries which may likely to be caused by the movement pattern or the performance of the physical activity. Customized suggestions may be provided to the athlete to overcome such injuries.

Figure 1:
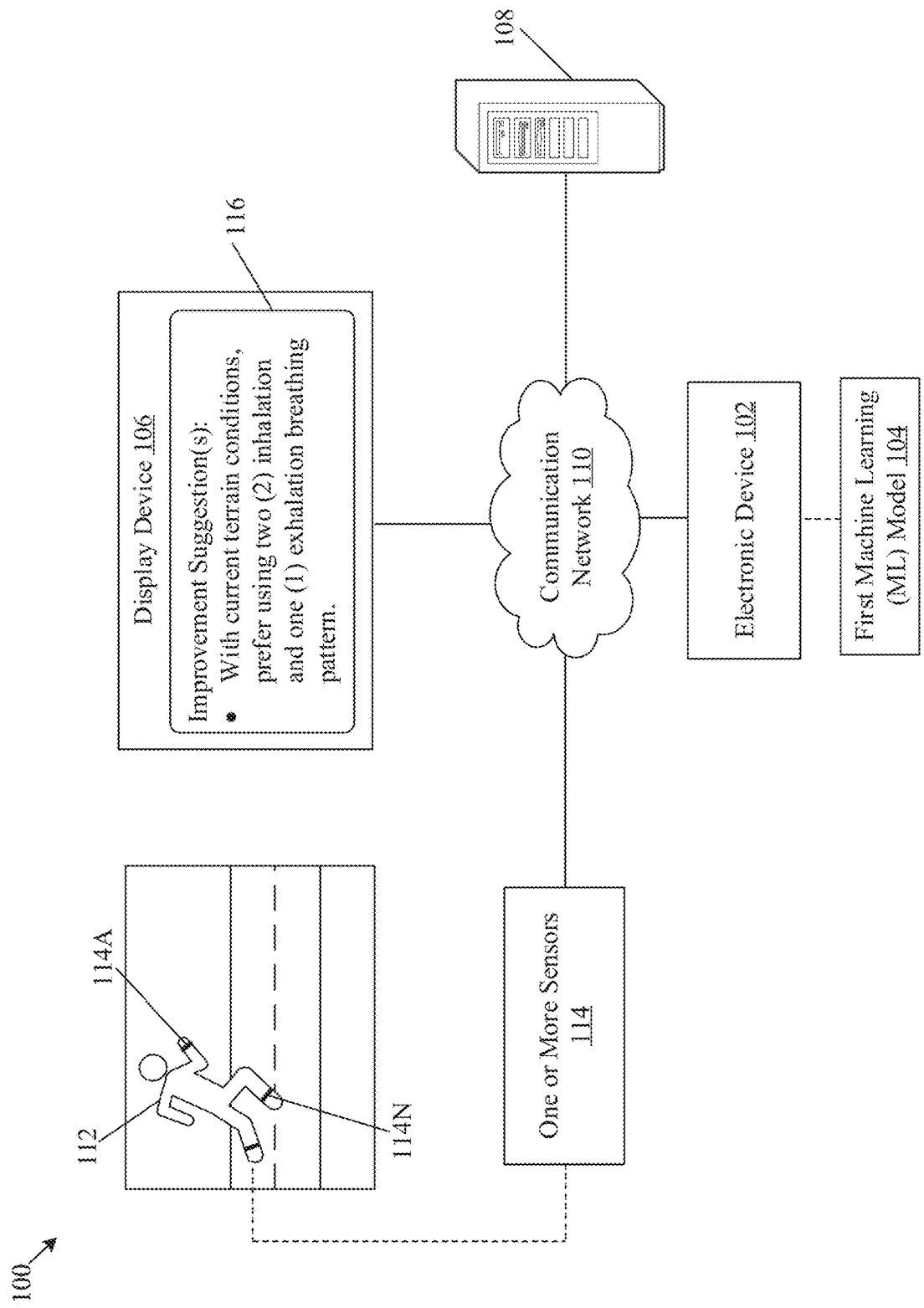
FIG. 1 is a block diagram that illustrates an exemplary network environment for data-driven assistance for users involved in physical activities, in accordance with an embodiment of the disclosure.

FIG. 1 is a block diagram that illustrates an exemplary network environment for data-driven assistance for users involved in physical activities, in accordance with an embodiment of the disclosure. With reference to FIG. 1, there is shown a network environment 100. The network environment 100 may include an electronic device 102, a first machine learning (ML) model 104, a display device 106, a server 108, and a communication network 110. The electronic device 102 may be communicatively coupled to the first ML model 104, the display device 106, and the server 108, via the communication network 110.

In FIG. 1, the first ML model 104 is shown as separate from the electronic device 102. However, the disclosure may not be so limiting and in some embodiments, the first ML model 104 may be included in the electronic device 102, without departing from scope of the disclosure. With reference to FIG. 1, there is further shown a user 112. The user 112 may be an athlete or a trainee who performs or trains for a physical activity. There is further shown one or more sensors 114. In an embodiment, the one or more sensors 114 may be worn by the user 112, while the user 112 performs the physical activity. For example, the user 112 may wear a first sensor 114A and an Nth sensor 114N on the arms and the legs, respectively. In another embodiment, the one or more sensors 114 may be placed close to or ambient to a location where the user 112 performs the physical activity. In another embodiment, the one or more sensors 114 may be integrated into the electronic device 102.

The electronic device 102 may include suitable logic, circuitry, interfaces, and or code that may be configured to provide data-driven assistance to users (such as the user 112) involved in physical activities. Such an assistance may be provided through improvement suggestions in relation to the physical activities so that the athletes may avoid injuries and enhance their performance in the physical activities. Examples of the electronic device 102 may include, but are not limited to, a wearable electronic device (such as a smartwatch, a wearable health monitoring device, an activity tracker, and smart glasses), a head-mounted display (such as an eXtended Reality (XR) device), a computing device, a personal computer, a computer work-station, a mainframe computer, a handheld computer, a smartphone, a cellular phone, a gaming device, a server, and/or other computing devices with data processing capability.

The first ML model 104 may be a model that may be trained to analyze data associated with the user 112 and to output various results in the form of recommendation results, classification results, clustering results, regression or prediction results, and/or a combination thereof. In an embodiment, the first ML model 104 may be a computational network or a system of artificial neurons or as nodes, arranged in a plurality of layers. The plurality of layers of the first ML model 104 may include an input layer, one or more hidden layers, and an output layer. Each layer of the plurality of layers may include one or more nodes (or artificial neurons, represented by circles, for example). Outputs of all nodes in the input layer may be coupled to at least one node of hidden layer(s). Similarly, inputs of each hidden layer may be coupled to outputs of at least one node in other layers of the first ML model 104. Outputs of each hidden layer may be coupled to inputs of at least one node in other layers of the first ML model 104. Node(s) in the final layer may receive inputs from at least one hidden layer to output a result. The number of layers and the number of nodes in each layer may be determined from hyper-parameters of the first ML model 104. Such hyper-parameters may be set before, while training, or after training the first ML model 104 on a training dataset.

Each node of the first ML model 104 may correspond to a mathematical function (e.g., a sigmoid function or a rectified linear unit) with a set of parameters, tunable during training of the first ML model 104. The set of parameters may include, for example, a weight parameter, a regularization parameter, and the like. Each node may use the mathematical function to compute an output based on one or more inputs from nodes in other layer(s) (e.g., previous layer(s)) of the first ML model 104. All or some of the nodes of the first ML model 104 may correspond to same or a different mathematical function.

In training of the first ML model 104, one or more parameters of each node of the first ML model 104 may be updated based on whether an output of the final layer for a given input (from the training dataset) matches a correct result based on a loss function for the first ML model 104. The above process may be repeated for same or a different input until a minima of loss function is achieved, and a training error is minimized. Several methods for training are known in art, for example, gradient descent, stochastic gradient descent, batch gradient descent, gradient boost, meta-heuristics, and the like.

The first ML model 104 may include electronic data, which may be implemented as, for example, a software component of an application executable on the electronic device 102. The first ML model 104 may rely on libraries, external scripts, or other logic/instructions for execution by a processing device, such as electronic device 102. The first ML model 104 may include code and routines configured to enable a computing device, such as the electronic device 102 to perform one or more operations for generation of the presentation data 116. Additionally, or alternatively, the first ML model 104 may be implemented using hardware including, but not limited to, a processor, a microprocessor (e.g., to perform or control performance of one or more operations), a field-programmable gate array (FPGA), a co-processor, or an application-specific integrated circuit (ASIC). Alternatively, in some embodiments, the first ML model 104 may be implemented using a combination of hardware and software.

Examples of the first ML model 104 may include, but are not limited to, a Bayesian model, a decision tree, a Support Vector Machine, a deep neural network (DNN), a convolutional neural network (CNN), a recurrent neural network (RNN), an artificial neural network (ANN), a gated recurrent unit (GRU)-based RNN, a fully connected neural network, a deep Bayesian neural network, a hybrid DNN, and/or a combination of such networks.

The display device 106 may include suitable logic, circuitry, and interfaces that may be configured to display the generated presentation data 116. In an embodiment, the generated presentation data 116 may be displayed on an electronic user interface (UI) rendered on the display device 106. The display device 106 may be a touch screen which may enable a user to provide a user-input via the display device 106. The touch screen may be at least one of a resistive touch screen, a capacitive touch screen, or a thermal touch screen. The display device 106 may be realized through several known technologies such as, but not limited to, at least one of a Liquid Crystal Display (LCD) display, a Light Emitting Diode (LED) display, a plasma display, or an Organic LED (OLED) display technology, or other display devices. In accordance with an embodiment, the display device 106 may refer to a display screen of a head mounted device (HMD), a smart-glass device, a see-through display, a projection-based display, an electro-chromic display, or a transparent display.

The server 108 may include suitable logic, circuitry, interfaces, and code that may be configured to store user-specific data, such as but not limited to, a profile of the user 112, a set of anthropometric features, historical physical activity data, a demography to which the user 112 belongs, a preference for physical activities, a recent or current activity data, a set of recent or historical (e.g., in last few months or years) instances of medical attention or interventions required by the user 112, and data about existing medical conditions of the user 112. In some embodiments, the server 108 may store motion detection data, breathing data, and accelerometer data. In another embodiment, the first ML model 104 and a second ML model (not shown) may be trained and/or stored on the server 108.

In an embodiment, the server 108 may be implemented as a cloud server which may execute operations through web applications, cloud applications, HTTP requests, repository operations, file transfer, and the like. Other examples of the server 108 may include, but are not limited to a database server, a file server, a web server, a media server, an application server, a mainframe server, a cloud server, or other types of servers. In one or more embodiments, the server 108 may be implemented as a plurality of distributed cloud-based resources by use of several technologies that are well known to those skilled in the art. A person with ordinary skill in the art will understand that the scope of the disclosure may not be limited to implementation of the server 108 and the electronic device 102 as separate entities. In certain embodiments, the functionalities of the server 108 may be incorporated in its entirety or at least partially in the electronic device 102, without departure from the scope of the disclosure.

The communication network 110 may include a communication medium through which the electronic device 102, the display device 106, and the server 108 may communicate with each other. The communication network 110 may be a wired or wireless communication network. Examples of the communication network 110 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 110, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 1102.11, light fidelity(Li-Fi), 1102.16, IEEE 1102.11s, IEEE 1102.11g, multi-hop communication, wireless access point (AP), device to device communication, cellular communication protocols, and Bluetooth (BT) communication protocols.

Each of the one or more sensors 114 may include suitable logic, circuitry, and/or interfaces that may be configured capture sensor data that includes values related to one or more biological markers and/or biomechanics of the body of the user 112. Examples of such sensors may include, but are not limited to, a breathing rate sensor, a heart rate sensor, a blood pressure sensor, and an oxygen saturation sensor. In some embodiments, the one or more sensors 114 may be configured to measure the motion of one or more parts of the body of the user 112. Examples of such sensors may include, but are not limited to, an accelerometer, a motion sensor, a gyro sensor, a gait sensor, a high-rate Global Navigation Satellite System (GNSS) receiver, a foot pressure sensor. In some other embodiments, the one or more sensors 114 may include one or more image-capture devices placed around the user 112 at specific viewpoints. Such devices may capture a set of images of the user 112 while the user performs the physical activity.

In operation, the electronic device 102 may activate the one or more sensors 114 to capture sensor data associated with the user 112. The activation may be based on one or more trigger inputs. Such inputs may be received from the user 112 or may be triggered based on an activity schedule of the user 112 or a user preference preset on the electronic device 102. In an embodiment, the one or more sensors 114 may be self-activated based on detection of a movement pattern of the user 112, a user input, a pose/stance associated with a physical activity, or a presence of the user 112 at a location associated with the physical activity. As shown, for example, while performing the physical activity, the user 112 may wear the one or more sensors 114 (such as the first sensor 114A and/or the Nth sensor 114N). The physical activity may include, for example, running, dancing, swimming, gymnastics, tennis, hockey, basketball, cricket, tennis, table tennis, soccer, baseball, archery, badminton, volleyball, cycling, boxing, golf, handball, judo, karate, fencing, rowing, weight-lifting, shooting, and the like.

Based on activation, the one or more sensors 114 may capture first sensor data and second sensor data associated with a movement pattern of one or more parts of a body of the user 112. At any time-instant, the captured first sensor data and/or the second sensor data may be transmitted to the electronic device 102. In an embodiment, the data may be transmitted or streamed to the electronic device 102 in the same duration in which the user 112 may be perform the physical activity. In another embodiment, the data may be transmitted or streamed to the electronic device 102 based on a request from the electronic device 102 or after the performance of the user 112 is over.

The electronic device 102 may receive the captured first sensor data associated with the movement pattern of one or more parts of the body of the user 112. The first sensor data may correspond to a duration in which the user 112 performs the physical activity. The first sensor data may include, for example, first accelerometer data associated with the movement pattern of an arm portion, a leg portion, or a foot portion of the body of the user 112. The electronic device 102 may further receive first information associated with a location where the user 112 performs the physical activity. The received first information may include, for example, the location of the user 112, a ground elevation of the location, weather information associated with the location, terrain information associated with the location, and the like.

The electronic device 102 may be further configured to determine one or more first indicators, likely to have affected the user 112 or the performance of the user 112 in the physical activity. By way of example, and not limitation, if the physical activity is running or sprinting, then the first indicators may be related to posture, user's breathing cycle, the foot landing pattern, and the stride of the user 112. In an embodiment, the one or more indicators may be associated with one or more biological markers of the body of the user 112.

The electronic device 102 may be further configured to generate the presentation data 116 based on application of the first ML model 104 on the determined one or more first indicators and the received first information. In an embodiment, the first ML model 104 may be a pre-trained model that may be trained on data associated with an expert level athlete and/or an intermediate level athlete. In another embodiment, the first ML model 104 may be auto-trained on the data associated with an expert level athlete and/or an intermediate level athlete at or during run-time. The generated presentation data 116 may include one or more improvement suggestions for the user 112 in relation to the physical activity. In an embodiment, the presentation data may further include visual data which may be a comparison of the one or more first indicators with known indicators of expert athletes. Details about the one or more first indicators and the presentation data are provided, for example, in FIGS. 3A, 3B, 4A, 4B, 5A, 5B, 5C, 6, 7A, 7B, 8, 9A, 9B 10, 11A, 11B, and 12.

Based on the generation of the presentation data 116, the electronic device 102 may configured to control the display device 106. The display device 106 may be controlled to display the generated presentation data 116 on the electronic UI of the display device 106. In an embodiment, the electronic device 102 may be configured to render the one or more improvement suggestions for the user 112 via an audio reproduction device (not shown). For example, the user 112 may wear the audio reproduction device (for example, a headphone) while performing the physical activity.

Modifications, additions, or omissions may be made to FIG. 1 without departing from the scope of the present disclosure. For example, the network environment 100 may include more or fewer elements than those illustrated and described in the present disclosure. For instance, in some embodiments, the network environment 100 may include an audio rendering device and a haptic feedback device that can provide audible and haptic feedback to the user 112. For example, the audible feedback and/or the haptic feedback may be delivered to a smartwatch worn by the user 112 if the body posture of the user 112 is not correct.

Figure 2:
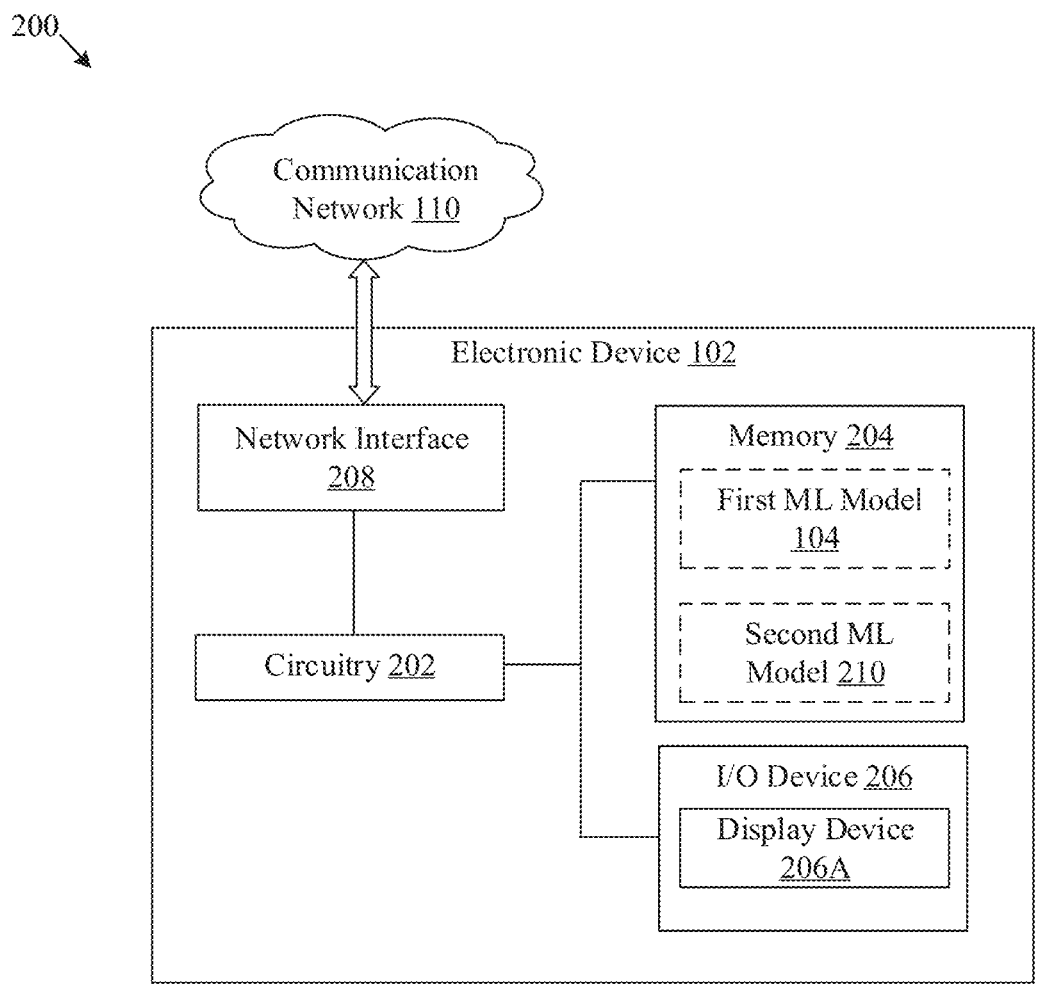
FIG. 2 is a block diagram that illustrates an exemplary electronic device for data-driven assistance for users involved in physical activities, in accordance with an embodiment of the disclosure.

FIG. 2 is a block diagram that illustrates an exemplary electronic device for data-driven assistance for users involved in physical activities, in accordance with an embodiment of the disclosure. FIG. 2 is explained in conjunction with elements from FIG. 1. With reference to FIG. 2, there is shown a block diagram 200 of the electronic device 102. The electronic device 102 may include circuitry 202 which may perform operations for generation of the presentation data 116. The electronic device 102 may further include a memory 204, an input/output (I/O) device 206, and a network interface 208. The memory 204 may include the first ML model 104 and a second machine learning (ML) model 210. The circuitry 202 may be communicatively coupled to the memory 204, the I/O device 206, and the network interface 208.

The circuitry 202 may include suitable logic, circuitry, and interfaces that may be configured to execute program instructions associated with different operations to be executed by the electronic device 102. For example, some of the operations may include reception of the first sensor data and the first information, determination of the one or more first indicators, generation of the presentation data 116, and displaying the generated presentation data 116. The circuitry 202 may include one or more specialized processing units, which may be implemented as a separate processor. In an embodiment, the one or more specialized processing units may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other control circuits.

The memory 204 may comprise suitable logic, circuitry, interfaces, and/or code that may be configured to store the instructions to be executed by the circuitry 202. The memory 204 may be configured to store the received first sensor data, the second sensor data, motion detection data, accelerometer data, and breathing data. In some embodiments, the memory 204 may be configured to store the one or more first indicators, one or more second indicators, and one or more third indicators. The memory 204 may be further configured to store the first ML model 104 and the second ML model 210. The memory 204 may be further configured to store the generated presentation data 116. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, and interfaces that may be configured to receive an input and provide an output based on the received input. The I/O device 206 may be configured to receive a first user input that may include the first sensor data, and/or the second sensor data. The I/O device 206 may be configured to display the presentation data 116 via the display device 106. The I/O device 206 which may include various input and output devices, which may be configured to communicate with the circuitry 202. Examples of the I/O device 206 may include, but are not limited to, the display device 106, an audio rendering device, a haptic feedback device, a touch screen, a keyboard, a mouse, a joystick, and a microphone.

The network interface 208 may include suitable logic, circuitry, and interfaces that may be configured to facilitate communication between the circuitry 202, the display device 106, and the server 108, via the communication network 110. The network interface 208 may be implemented by use of various known technologies to support wired or wireless communication of the electronic device 102 with the communication network 110. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry. The network interface 208 may be configured to communicate via wireless communication with networks, such as the Internet, an Intranet or a wireless network, such as a cellular telephone network, a wireless local area network (LAN), and a metropolitan area network (MAN). The wireless communication may be configured to use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 1102.11a, IEEE 1102.11b, IEEE 1102.11g or IEEE 1102.11n), voice over Internet Protocol (VoIP), light fidelity (Li-Fi), Worldwide Interoperability for Microwave Access (Wi-MAX), a protocol for email, instant messaging, and a Short Message Service (SMS).

The second ML model 210 may be a classifier model which may be trained to identify a relationship between inputs, such as features in a training dataset and output labels. The second ML model 210 may be defined by its hyper-parameters, for example, number of weights, cost function, input size, number of layers, and the like. The hyper-parameters of the second ML model 210 may be tuned and weights may be updated so as to move towards a global minima of a cost function for the second ML model 210. After several epochs of the training on the feature information in the training dataset, the second ML model 210 may be trained to output a classification result for a set of inputs.

The second ML model 210 may include electronic data, which may be implemented as, for example, a software component of an application executable on the electronic device 102. The second ML model 210 may rely on libraries, external scripts, or other logic/instructions for execution by a processing device, such as circuitry 202. The second ML model 210 may include code and routines configured to enable a computing device, such as circuitry 202 to perform one or more operations to determine an experience level of the user 112. Specifically, the second ML model 210 may classify the user 112 as one of an amateur level athlete, an intermediate level athlete, or an expert level athlete. Additionally, or alternatively, the second ML model 210 may be implemented using hardware including a processor, a microprocessor (e.g., to perform or control performance of one or more operations), a field-programmable gate array (FPGA), or an application-specific integrated circuit (ASIC). Alternatively, in some embodiments, the second ML model 210 may be implemented using a combination of hardware and software. Various operations of the circuitry 202 are described further, for example, in FIGS. 3A, 3B, 4A, 4B, 5A, 5B, 5C, 6, 7A, 7B, 8, 9A, 9B 10, 11A, 11B, and 12.

Figure 3A:
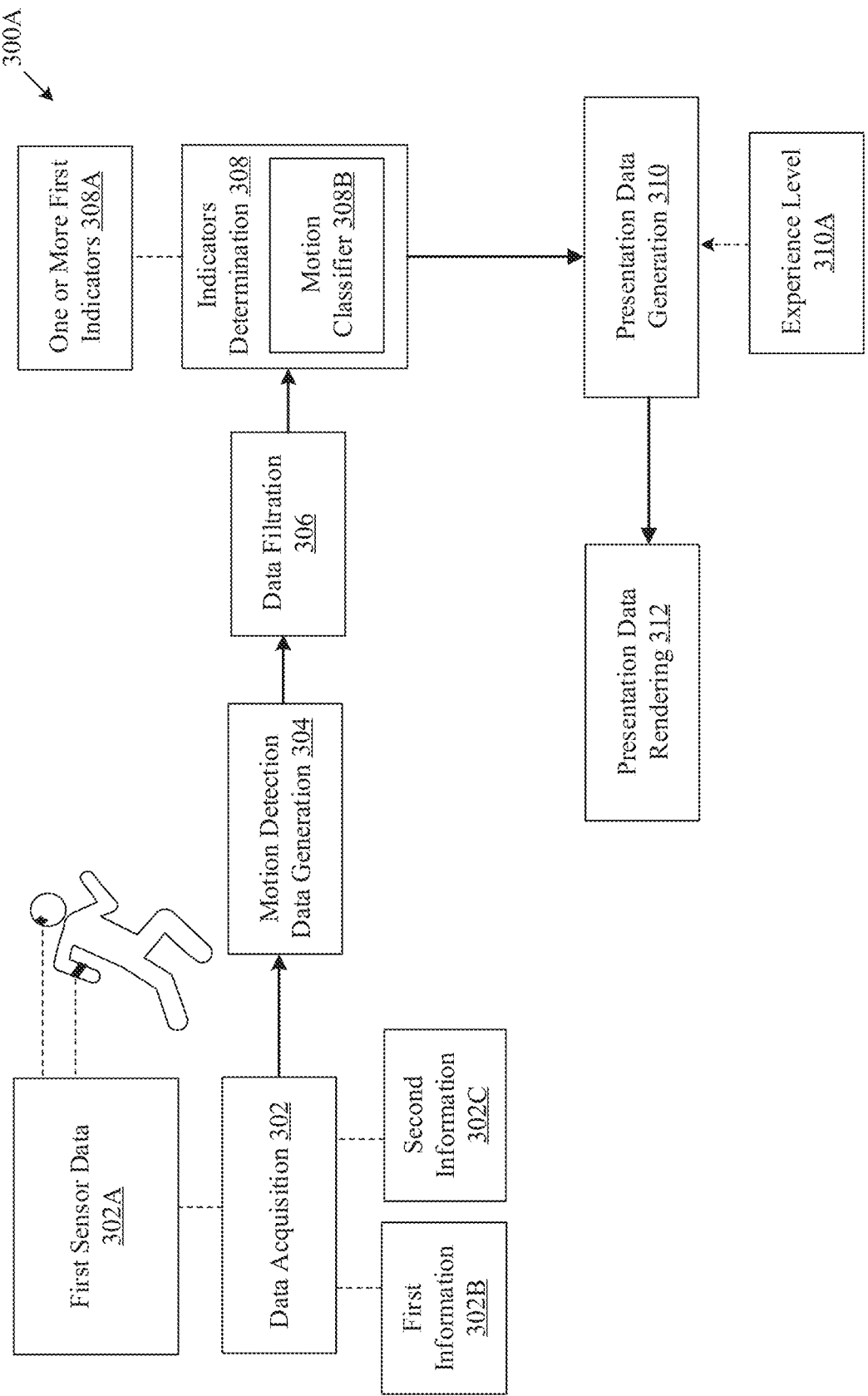
FIG. 3A is a diagram that illustrates exemplary operations for data-driven assistance to users involved in physical activities where a swing movement of the arm is required, in accordance with an embodiment of the disclosure.

FIG. 3A is a diagram that illustrates exemplary operations for data-driven assistance to users involved in physical activities where a swing movement of the arm is required, in accordance with an embodiment of the disclosure. FIG. 3A is explained in conjunction with elements from FIG. 1 and FIG. 2. With reference to FIG. 3A, there is shown a block diagram 300A that illustrates exemplary operations from 302 to 312, as described herein. The exemplary operations illustrated in the block diagram 300A may start at 302 and may be performed by any computing system, apparatus, or device, such as by the electronic device 102 of FIG. 1 or circuitry 202 of FIG. 2. Although illustrated with discrete blocks, the exemplary operations associated with one or more blocks of the block diagram 300A may be divided into additional blocks, combined into fewer blocks, or eliminated, depending on the particular implementation.

At 302, a data acquisition operation may be performed. In the data acquisition operation, the circuitry 202 may be configured to receive first sensor data 302A associated with a movement pattern of one or more parts of the body of the user 112. The first sensor data 302A may be captured by the first sensor 114A of the one or more sensors 114 and may be worn by the user 112. In an embodiment, the first sensor 114A may be an accelerometer sensor that may be worn on the arm of the user 112 and may capture the first sensor data 302A for a duration in which the user 112 performs the physical activity data (such as a running activity). The captured first sensor data 302A may include first accelerometer data associated with the movement pattern of the arm portion of the body of the user 112. Additionally, or alternatively, the captured first sensor data 302A may include second accelerometer data about a movement pattern of a head portion and a shoulder portion of the user 112.

In an embodiment, the circuitry 202 may be further configured to receive first information 302B associated with the location where the user 112 performs the physical activity. The first information 302B may include, for example, weather information and terrain information associated with the location. The weather information may include information about temperature, humidity or precipitation, atmospheric pressure, solar radiation, wind speed, and the like. The terrain information may include information about elevation, inclination, declination, and type of track/soil associated with the corresponding location.

In an embodiment, the circuitry 202 may be configured to receive second information 302C associated with the performance of the user 112 in the physical activity. In an embodiment, the second information 302C may be received through a user input. The performance data may include historical performance data and current performance data in the same physical activity. For example, for the running activity, the performance data may include an average speed or a timeseries of speed values (in feet or meters per second), instances of injury or medical attention, a distance covered at the average speed, a comparison of the speed or distance covered with past records of speed or distance values, and the like. The performance of the user 112 may be determined based on the collected first sensor data 302A, an input from a user (such as a coach or trainer), a set of results generated by a performance tracking system, and/or a combination thereof. The performance tracking system may be a software application or a specialized device that logs the performance data of the user 112 while the user 112 performs the physical activity. As a software application, the performance tracking system may be implemented on a server or locally on a computing device associated with the user 112 or a coach/trainer associated with the user 112.

At 304, motion detection data may be generated. The circuitry 202 may be configured to generate motion detection data associated with the movement pattern of the arm portion and/or other body parts of the user 112. The motion detection data may be generated based on an analysis of the received first sensor data 302A and may include a plurality of samples, each of which may correspond to a motion parameter (such as a direction of motion, a rate of change in position, a position, an orientation, and a displacement) associated with one of the arm portion, the head portion, and/or the shoulder portion of the user 112. Examples of the motion detection data may include, but are not limited to, a rate of motion of the arm portion, a direction of motion of the arm portion, a pose (in terms of roll, yaw, and pitch) of the head portion, and a relative position or orientation of the shoulder with respect to the arm portion.

At 306, a data filtration operation may be performed. In the data filtration operation, the circuitry 202 may be configured to filter the generated motion detection data by removal of a first set of outlier samples from the generated motion detection data. In an embodiment, the filtering may include application of a clustering operation, such as an unsupervised machine-learning based clustering on the plurality of samples (included in the motion detection data). Application of the clustering operation may result in a set of clusters of samples. From the motion detection data, samples not in any of the set of clusters may be treated as the first set of outlier samples. Each of the first set of outlier samples may vary significantly from other samples in the generated motion detection data. For example, the distance of outlier samples associated with the arm portion from other samples in the clusters may be above a threshold. Such outlier samples may be removed from the motion detection data.

At 308, one or more indicators may be determined. The circuitry 202 may be configured to determine one or more first indicators 308A by application of a motion classifier 308B on the filtered motion detection data. In an embodiment, the motion classifier 308B may be a first neural network (NN) model that may be trained to determine a type of activity performed by the user 112 based on the filtered motion detection data.

The one or more first indicators 308A may be likely to have affected the user 112 or the performance of the user 112 in the physical activity. By way of example, and not limitation, the effect on the user 112 may be in terms of indicators, such as a fitness level, a number of times the user 112 suffered an injury in the duration in which the user 112 performed the physical activity, a type of injury that the user suffered, and one or more instances in which the user 112 required any kind of medical attention in the duration in which the user 112 performed the physical activity.

The effect on the performance may be in terms of indicators, such as a duration for which the user performed the physical activity, or a label predicted by the motion classifier 308B based on the filtered motion detection data. For example, for a duration of 10 minutes of the physical activity, the motion classifier 308B may be applied on the filtered motion data to determine the one or more first indicators 308A. Such indicators 308A may classify the physical activity performed by the user 112 as running for 2 minutes, resting for 5 minutes, and walking for 3 minutes. Along with the indicators, the motion detection data may be analyzed to generate a trajectory of the arm portion, the shoulder portion, and the head portion. Each of the determined indicators may be processed to further analyze the impact/effect on the user 112 (such as on a fitness level or a stance/form of the user 112) and/or the performance of the user 112.

At 310, a presentation data generation operation may be performed. In the presentation data generation operation, the circuitry 202 may be configured to generate presentation data based on application of the first ML model 104 on the determined one or more first indicators 308A, the received first information 302B, and the received second information 302C (includes the performance data of the user 112).

In an embodiment, the circuitry 202 may generate the presentation data further based on an experience level 310A of the user 112. The experience level 310A may be used for comparison of the performance or specific performance-indicators of the user 112 with that of an expert athlete. An example of such a comparison is provided in FIG. 3B. In an embodiment, to determine the experience level 310A, the circuitry 202 may be configured to apply the second ML model 210 on the determined one or more first indicators 308A and the received first information 302B to generate a classification result. The classification result may include one or more labels that identify the user 112 as one of an amateur athlete, an intermediate or average athlete, or an expert athlete. The circuitry 202 may be further configured to determine the experience level 310A of the user 112 in relation to the physical activity, based on the classification result. The determined experience level 310A may be one of an amateur athlete, an intermediate or average athlete, or an expert athlete.

In another embodiment, the generated presentation data may include one or more improvement suggestions for the user 112 in relation to the physical activity. The one or more improvement suggestions may be associated with a swing movement of the arm portion of the user 112. Additionally, or alternatively, the improvement suggestions may be associated with a movement of the shoulder portion and/or a posture of the head portion of the user 112. Such suggestions may prompt or inform the user 112 about measures to correct the way the user 112 performs the physical activity. For example, such measures prompt the user 112 to correct the head pose to match that of an expert athlete while running, to correct the position of the shoulder, or to adjust the swing movement of the arm to match that of the expert athlete. In an embodiment, the generated presentation data may include visual data that may include a comparison of the swing movement of the arm portion of the user 112 with a swing movement of the arm portion of an expert athlete.

In an embodiment, the circuitry 202 may be configured to determine one or more injuries, which may be likely to be caused by the movement pattern or the performance in the physical activity. The one or more injuries may be determined based on analysis of the determined one or more first indicators. The generated presentation data may include information which informs the user 112 about the one or more injuries and recommendations to avoid the one or more injuries. The details about the presentation data are provided, for example, in FIG. 3B.

At 312, a presentation data rendering operation may be performed. In the presentation data rendering operation, the circuitry 202 may be configured to control the display device 106 to display the generated presentation data. In an embodiment, the presentation data may be displayed on an electronic user Interface (UI) that may be rendered on a display screen of the display device 106, as described in FIG. 3B, for example.

Figure 3B:
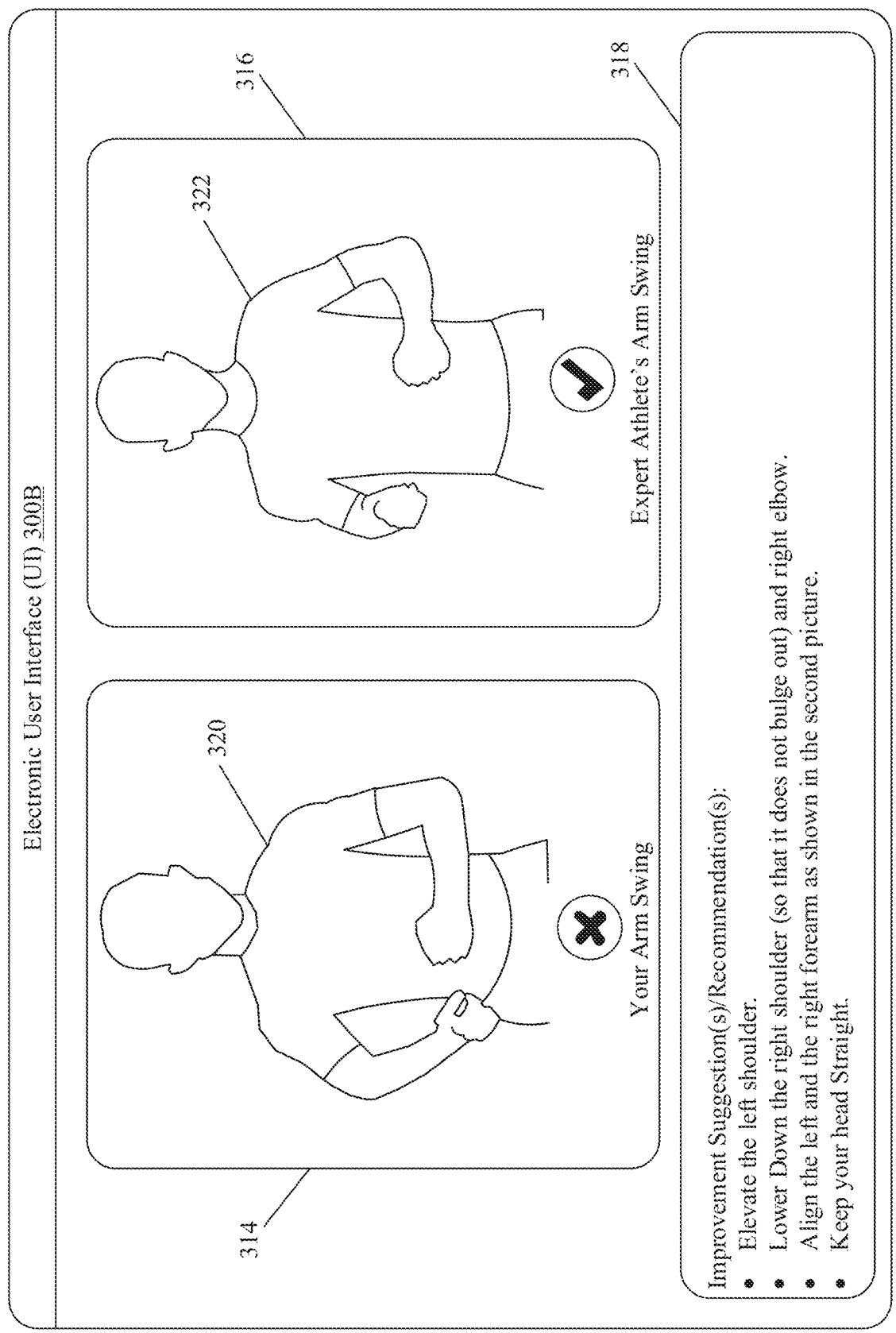
FIG. 3B is a diagram that illustrates an example electronic user interface for rendering of presentation data generated in FIG. 3A, according to at least one embodiment described in the present disclosure.

FIG. 3B is a diagram that illustrates an example of presentation data generated based on operations of FIG. 3A, in accordance with at least one embodiment described in the present disclosure. FIG. 3B is explained in conjunction with elements from FIG. 1, FIG. 2, and FIG. 3A. With reference to FIG. 3B, there is shown an electronic UI 300B. The electronic UI 300B may be displayed on the display device 106 and may be part of an application interface displayed onto a display screen of the display device 106. The application interface may be part of an application software, for example, a software development kit (SDK), a cloud server-based application, a web-based application, an OS-based application/application suite, an enterprise application, or a mobile application.

On the electronic UI 300B, there is shown a set of UI elements, such as a first UI element 314, a second UI element 316, and a third UI element 318. On the first UI element 314, a first image of a user 320 performing the physical activity may be displayed. On the second UI element 316, a second image of an expert athlete 322 performing the physical activity may be displayed. The first image of the user 320 and the second image of the expert athlete 322 may be displayed so that the user 320 can compare the swing movement and a position of the arm portion and other parts, such as the shoulder or the head portion of the expert athlete 322 with his/her own swing movement and the position of the arm portion and other parts.

The third UI element 318 may be a text box and may display the one or more improvement suggestions or recommendation(s) to the user 320. The one or more improvement suggestions or recommendation(s) may be associated with the swing movement of the arm portion and other body parts such as the shoulder and the head portion of the user 320. By way of example, and not limitation, the one or more improvement suggestions or recommendation(s) may include suggestions to "Elevate the left shoulder", "Lower Down the right shoulder (so that it does not bulge out) and right elbow" and "Align the left and the right forearm as shown in the second picture". In an embodiment, the third UI element 318 may include information about the one or more injuries and one or more recommendations to avoid the one or more injuries.

Figure 4A:
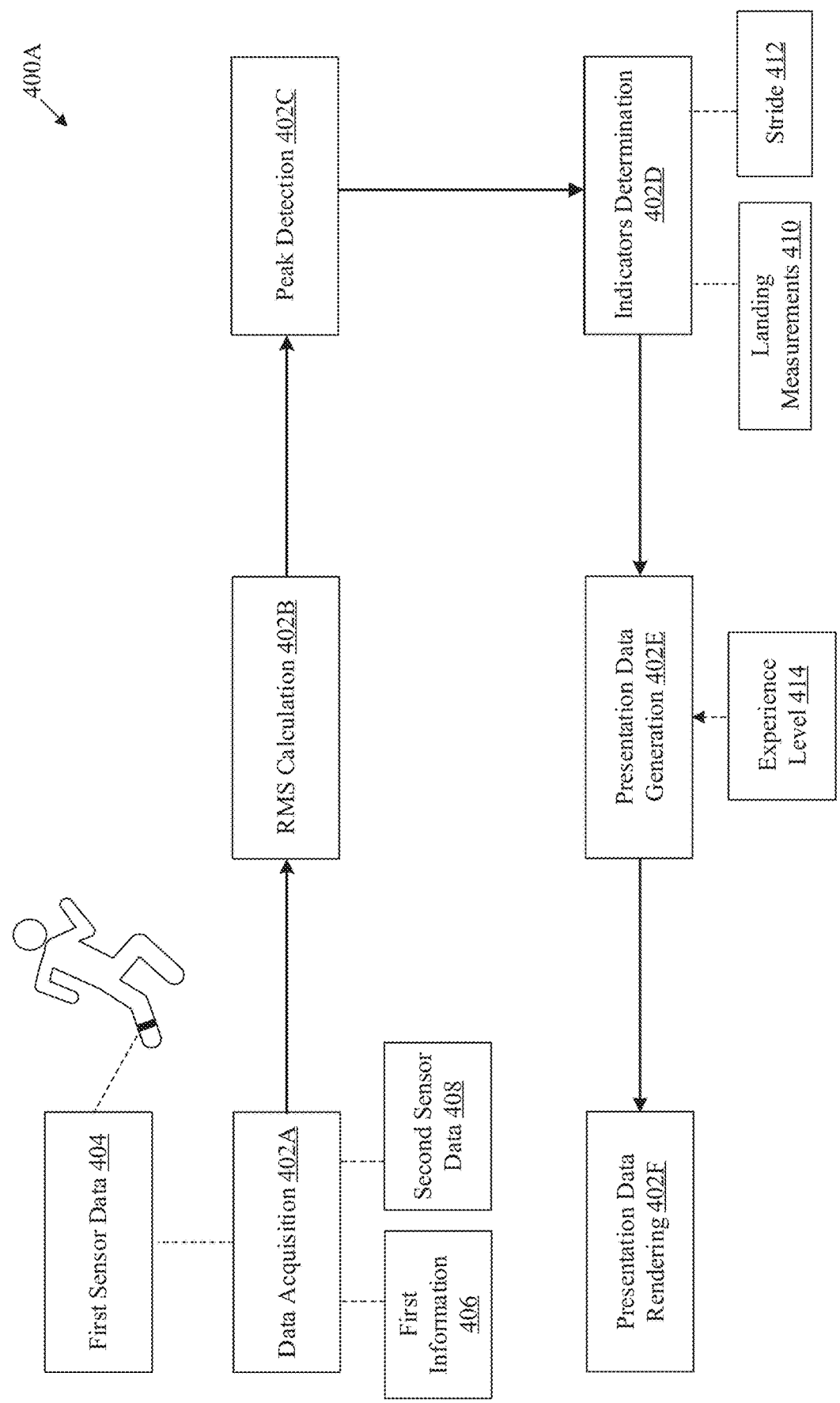
FIG. 4A is a diagram that illustrates exemplary operations for providing data-driven assistance to users involved in physical activities where a movement of the foot portion is required, in accordance with an embodiment of the disclosure.

FIG. 4A is a diagram that illustrates exemplary operations for providing data-driven assistance to users involved in physical activities where a movement of the foot portion is required, in accordance with an embodiment of the disclosure. FIG. 4A is explained in conjunction with elements from FIG. 1, FIG. 2, FIG. 3A, and FIG. 3B. With reference to FIG. 4A, there is shown a block diagram 400A that illustrates exemplary operations from 402A to 402F, as described herein. The exemplary operations illustrated in the block diagram 400A may start at 402A and may be performed by any computing system, apparatus, or device, such as by the electronic device 102 of FIG. 1 or circuitry 202 of FIG. 2. Although illustrated with discrete blocks, the exemplary operations associated with one or more blocks of the block diagram 400A may be divided into additional blocks, combined into fewer blocks, or eliminated, depending on the particular implementation.

At 402A, a data acquisition operation may be performed. As part of the data acquisition operation, the circuitry 202 may be configured to receive first sensor data 404 associated with the movement pattern of one or more parts of the body of the user 112. The first sensor data 404 may be captured by sensors (such as the one or more sensors 114) worn by the user 112 or placed around the user 112, while the user 112 performs the physical activity.

In an embodiment, the sensors may include an accelerometer sensor that may be worn on the leg portion of the user 112. The sensor may capture the first sensor data 404 for a duration in which the user 112 performs the physical activity (such as a running activity). The captured first sensor data 404 may include second accelerometer data associated with the movement pattern of a foot portion of the body. Specifically, the first sensor data 404 may include a series of X, Y, Z values indicating an articulate movement of the leg portion along X-axis, Y-axis, and Z-axis. The sensors may be configured to transfer the captured first sensor data 404 to the electronic device 102, via the communication network 110. In addition to the second sensor data 408, the circuitry 202 may be configured to receive first information 406 associated with a location where the user 112 performs the physical activity. As already discussed in FIG. 3A, the first information 406 may include weather information and terrain information associated with the location where the user 112 performs the physical activity.

In an embodiment, the circuitry 202 may be further configured to receive second sensor data 408. The second sensor data 408 may include one or more biological markers of the body of the user 112. Examples of such biological markers may include, but are not limited to, an oxygen saturation rate, a body temperature, a breathing rate, a blood pressure of the user 112. In an embodiment, the second sensor data 408 may be captured by sensors which may be different from the sensors (such as the one or more sensors 114) that acquire the first sensor data 404.

At 402B, root-mean square (RMS) values may be calculated. The circuitry 202 may be configured to calculate RMS values of acceleration based on the first sensor data 404. The RMS values of the acceleration ($G_{rms}$) may be defined as a square root of an area under an acceleration spectral density (ASD) curve in frequency domain. The $G_{rms}$ value may be used to express an overall energy of a particular event (such as the foot movement).

At 402C, a peak detection operation may be performed. In the peak detection operation, the circuitry 202 may be configured to detect peak values in the second sensor data 408. The peak values may be detected based on one or more peak detection methods, the detailed implementation of which may be known to one skilled in the art. A detailed description of such peak detection methods has been omitted from the disclosure for the sake of brevity.

At 402D, one or more first indicators, likely to have affected the user 112 or the performance of the user 112 in the physical activity may be determined. In an embodiment, the circuitry 202 may apply one or more signal processing operations on the second accelerometer data (part of the received first sensor data 404) to determine the one or more first indicators. In an embodiment, such operations may include the RMS values calculation of 402B and the peak detection operation of 402C.

The one or more indicators may include landing measurements 410 associated with the foot portion and a stride 412 (also referred to as a running stride) of the user 112. The landing measurements 410 may include, for example, a distribution of stress on the foot portion of the user 112 when the foot lands on the ground while performing the physical activity. The distribution of stress on the foot portion may be linked to supination and pronation of the stride 412. Supination typically occurs when the user 112 places the weight of the foot portion outside of the foot portion while walking or running. On the contrary, pronation may occur when the user 112 shifts the weight of the foot portion from the heel to the forefoot. An incorrect stress distribution may be linked to excessive supination or excessive pronation, which may affect the alignment of the body of the user 112 while performing the physical activity. In some instances, the incorrect stress distribution may lead to pain or injury in the foot, knees, hips, and back. Without corrective measures, any injury or any misalignment of the body may affect the fitness level of the user 112 and/or may affect the performance of the user 112 as well in the physical activity.

At 402E, presentation data may be generated. The circuitry 202 may be configured to generate the presentation data based on application of the first ML model 104 on the determined one or more first indicators and the received first information 406. Additionally, or alternatively, the presentation data may be generated based on application of the first ML model 104 on the second sensor data 408. An example of the presentation data is provided, for example, in FIG. 4B. The generated presentation data may include one or more improvement suggestions for the user 112 in relation to the physical activity. Specifically, the one or more improvement suggestions may be associated with the movement pattern of the foot portion of the user 112.

In an embodiment, the generated presentation data may include a comparison of the movement pattern of the foot portion of the user 112 with a first movement pattern of the foot portion of an expert athlete. For such comparison, the circuitry 202 may determine an experience level of the user 112 in the physical activity. The experience level may be used for comparison of the performance or specific performance-indicators of the user 112 with that of an expert athlete. In an embodiment, to determine the experience level, the circuitry 202 may be configured to apply the second ML model 210 on the determined one or more first indicators and the received first information 302B to generate a classification result. The classification result may include one or more labels that identify the user 112 as one of an amateur athlete, an intermediate or average athlete, or an expert athlete. The circuitry 202 may be configured to determine the experience level of user 112 in relation to the physical activity, based on the classification result.

At 402F, a presentation data rendering operation may be performed. In the presentation data rendering operation, the circuitry 202 may be configured to control the display device 106 to display the generated presentation data. In an embodiment, the presentation data may be displayed on an electronic user Interface (UI) that may be rendered on a display screen of the display device 106, as described in FIG. 4B.

Figure 4B:
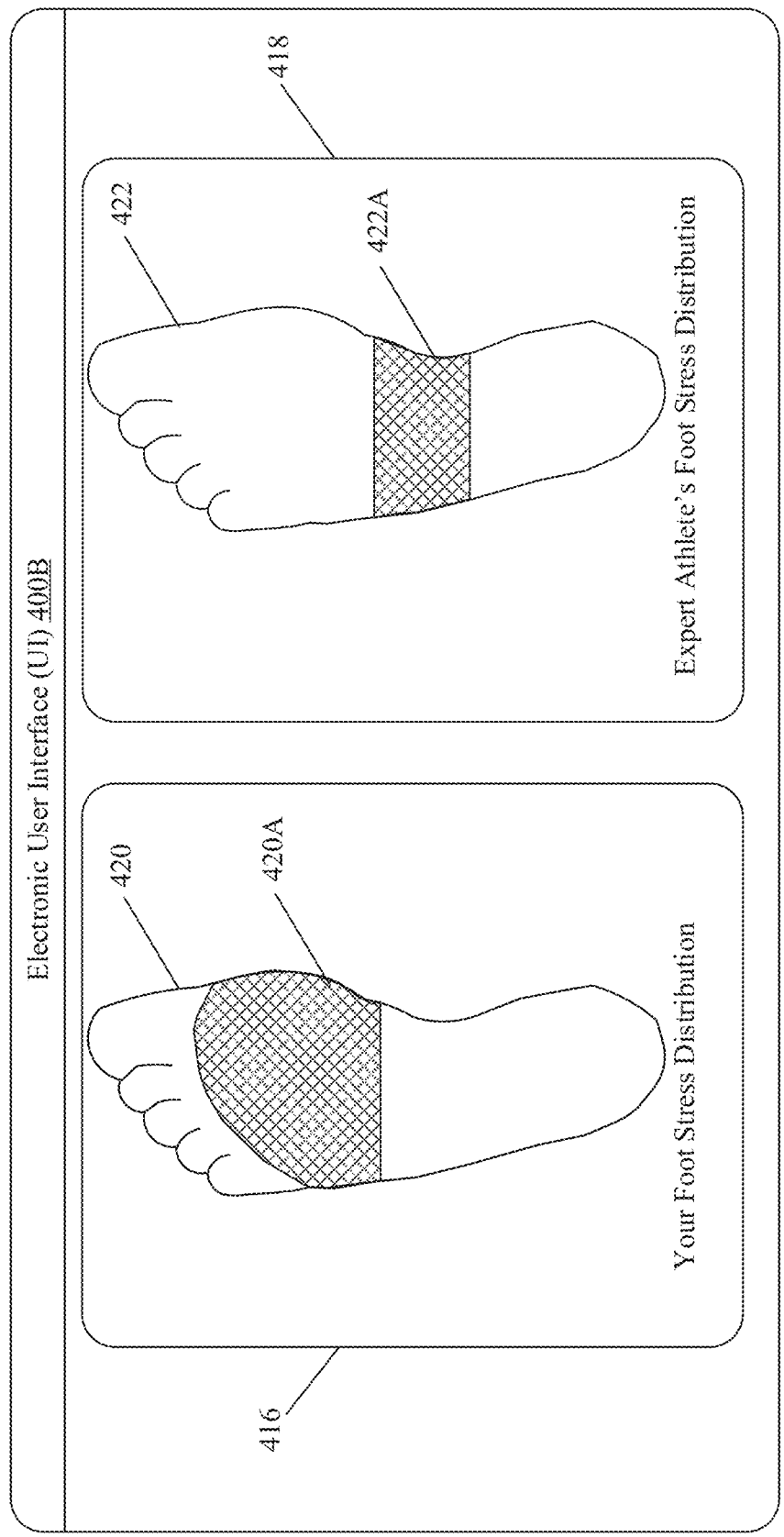
FIG. 4B is a diagram that illustrates an example electronic user interface for rendering of presentation data generated in FIG. 4A, according to at least one embodiment described in the present disclosure.

FIG. 4B is a diagram that illustrates an example electronic user interface for rendering of presentation data generated in FIG. 4A, according to at least one embodiment described in the present disclosure. FIG. 4B is explained in conjunction with elements from FIG. 1, FIG. 2, FIG. 3A, FIG. 3B, and FIG. 4A. With reference to FIG. 4B, there is shown an electronic UI 400B. The electronic UI 400B may be displayed on the display device 106. The electronic UI 400B may part of an application interface displayed onto a display screen of the display device 106. The application interface may be part of an application software, for example, a software development kit (SDK), a cloud server-based application, a web-based application, an OS-based application/application suite, an enterprise application, or a mobile application.

On the electronic UI 400B, there is shown a set of UI elements, such as a first UI element 416 and a second UI element 418. On the first UI element 416, a first image of a first sole 420 of the foot of the user 112 (while performing the physical activity) is displayed. On the second UI element 418, a second image of a second sole 422 of the foot of an expert athlete (while performing the physical activity) is displayed. In the first image, a first stress distribution area 420A may be highlighted with a specific color or gradient. Similarly, in the second image, a second stress distribution area 422A may be highlighted with a specific color or gradient. As shown, for example, the stress may be distributed on an upper part of the first sole 420 of the foot as depicted by the first stress distribution area 420A. For the expert athlete, the stress may be distributed on the middle part of the second sole 422 of the foot, as depicted by the second stress distribution area 422A.

In an embodiment, the presentation data may further include a third UI element (not shown) that may display one or more suggestions to modify the foot landing pattern in such a way that the stress is distributed evenly in the middle part of the first sole 420. Details of such one or more suggestions are omitted from the disclosure for the sake of brevity.

Figure 5A:
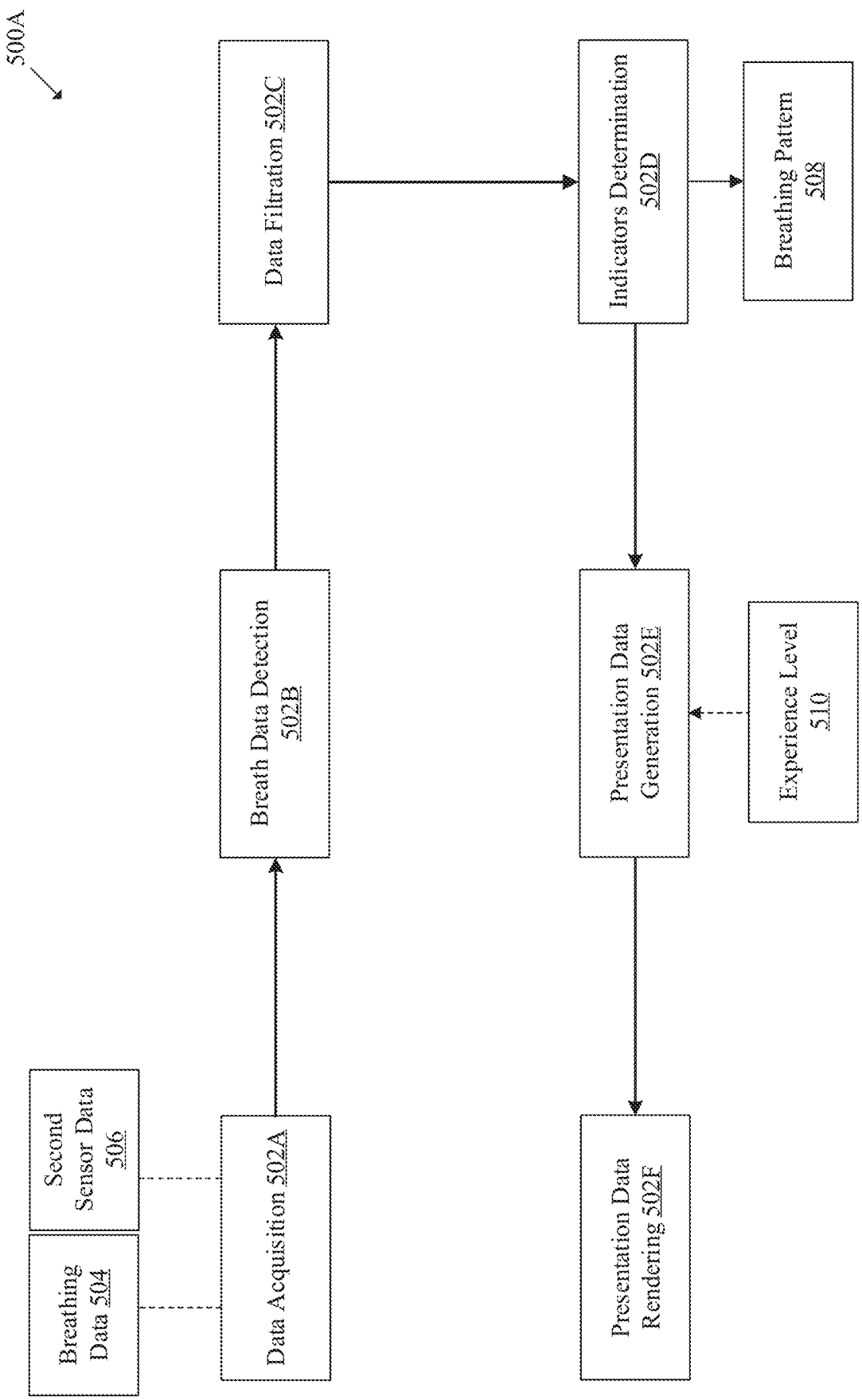
FIG. 5A is a diagram that illustrates exemplary operations for data-driven assistance for users involved in physical activities where a control over breathing is required, in accordance with an embodiment of the disclosure.

FIG. 5A is a diagram that illustrates exemplary operations for data-driven assistance for users involved in physical activities where a control over breathing is required, in accordance with an embodiment of the disclosure. FIG. 5A is explained in conjunction with elements from FIG. 1, FIG. 2, FIG. 3A, FIG. 3B, FIG. 4A, and FIG. 4B. With reference to FIG. 5A, there is shown a block diagram 500A that illustrates exemplary operations from 502A to 502F, as described herein. The exemplary operations illustrated in the block diagram 500A may start at 502A and may be performed by any computing system, apparatus, or device, such as by the electronic device 102 of FIG. 1 or circuitry 202 of FIG. 2. Although illustrated with discrete blocks, the exemplary operations associated with one or more blocks of the block diagram 500A may be divided into additional blocks, combined into fewer blocks, or eliminated, depending on the particular implementation.

At 502A, a data acquisition operation may be performed. In the data acquisition operation, the circuitry 202 may be configured to receive breathing data 504 associated with the user 112. The breathing data 504 may correspond to a duration in which the user 112 may perform the physical activity. In an embodiment, a breathing rate sensor (included in the one or more sensors 114) may be worn by the user 112. The breathing rate senor may capture the breathing data 504 of the user 112. In another embodiment, a microphone may be placed near the nose of the user 112. The microphone may capture audio data associated with a breathing sound produced by the user 112 while performing the physical activity. The audio data may be processed to generate the breathing data 504 in the form of digital audio samples. Multiple instances of both inspiration and expiration may be captured in the breathing data 504.

In addition to the breathing data 504, the circuitry 202 may be configured to receive second sensor data 506. The second sensor data 506 may include one or more biological markers of the body of the user 112. Examples of such biological markers may include, but are not limited to, an oxygen saturation rate, a body temperature, and a blood pressure of the user 112. In an embodiment, sensors which capture the second sensor data 506 may be different from the sensor that captures the breathing data 504. Along with the breathing data 504 and the second sensor data 506, the circuitry 202 may be configured to receive first information associated with the location where the user 112 performs the physical activity. Details about the first information are provided, for example, in FIG. 3A and FIG. 4A.

At 502B, breath detection data may be generated. The circuitry 202 may be configured to process the received breathing data 504 to generate the breath detection data. The breath detection data may include values which indicate instances of inhalation and exhalation within the duration in which the user 112 performed the physical activity. For each of such values, the breath detection data may also include a timestamp at which the inhalation or the exhalation occurred and/or a duration of the inhalation or exhalation. While a lower duration may mean a faster breathing rate, a higher duration may mean a lower breathing rate.

At 502C, a data filtration operation may be performed. In the data filtration operation, the circuitry 202 may be configured to filter the generated breath detection data by removal of a second set of outlier samples from the generated breath detection data. Each of the second set of outlier samples may correspond to instances of inhalation and/or exhalation that vary significantly from other samples of the generated breath detection data. For example, if a breath or an inhalation/exhalation phase is detected to be too close (for example, within 1 or 1.5 seconds) in time to a preceding or a succeeding breath or inhalation/exhalation phase, then such an instance of breath or inhalation/exhalation phase may be determined as an outlier sample.

At 502D, one or more second indicators, likely to have affected the user 112 or the performance of the user 112 in the physical activity may be determined. The circuitry 202 may be configured to determine the one or more second indicators by application of a breathing rate classifier on the filtered breath detection data. In an embodiment, the breathing classifier may be a second neural network (NN) model that may be trained to determine a breathing pattern 508 of the user 112 based on the filtered breath detection data. The one or more second indicators may include the breathing pattern 508 of the user 112. The breathing pattern 508 may include variations in tidal volume and a respiratory rate of the user 112 within the duration in which user 112 performed the physical activity. As an example, the breathing pattern 508 may correspond to an average breath rate of 16 breaths per minute at an average of 550 mL per breath. In an embodiment, the one or more second indicators may include classification of a breathing type of the user 112 as one of several types, such as eupnea, hyperpnea, diaphragmatic, costal, nasal breathing, or mouth breathing. Additionally, or alternatively, the one or more second indicators may include an indication of thoracic wall compliance, which may measure the ability of the thoracic wall of the user 112 to stretch while under pressure.

In an embodiment, the landing measurements 410 of the foot portion and the stride 412 of the user 112 (as described in FIG. 4A) may be analyzed together with the filtered breath detection data to determine an indicator which specifies whether or not the breathing pattern 508 of the user 112 is rhythmic. The indicator may be included in the one or more second indicators.

At 502E, a presentation data generation operation may be performed. In the presentation data generation operation, the circuitry 202 may be configured to generate presentation data based on application of the first ML model 104 on the determined one or more second indicators, the received second sensor data 506, and the received first information. The generated presentation data may include one or more improvement suggestions for the user 112 in relation to the physical activity. In an embodiment, the one or more improvement suggestions may be associated with the breathing pattern 508 of the user 112. In another embodiment, the one or more improvement suggestions may be associated with the oxygen saturation rate, the body temperature, and/or the blood pressure of the user 112.

In an embodiment, the generated presentation data may include a comparison of the breathing pattern 508, the oxygen saturation rate, the body temperature, and/or the blood pressure of the user 112 with that of an expert athlete. Examples of such presentation data are provided, for example, in FIGS. 5B and 5C. For such comparison, the circuitry 202 may determine an experience level 510 of the user 112 in the physical activity. The experience level 510 may be used for comparison of the performance or specific performance-indicators of the user 112 with that of an expert athlete. In an embodiment, to determine the experience level 510, the circuitry 202 may be configured to apply the second ML model 210 on the determined one or more first indicators and the received first information 302B to generate a classification result. The classification result may include one or more labels that identify the user 112 as one of an amateur athlete, an intermediate or average athlete, or an expert athlete. The circuitry 202 may be configured to determine the experience level 510 of user 112 in relation to the physical activity, based on the classification result.

At 502F, a presentation data rendering operation may be performed. In the presentation data rendering operation, the circuitry 202 may be configured to control the display device 106 to display the generated presentation data. In an embodiment, the presentation data may be displayed on an electronic user Interface (UI) that may be rendered on a display screen of the display device 106, as described in FIG. 5B and FIG. 5C.

Figure 5B:
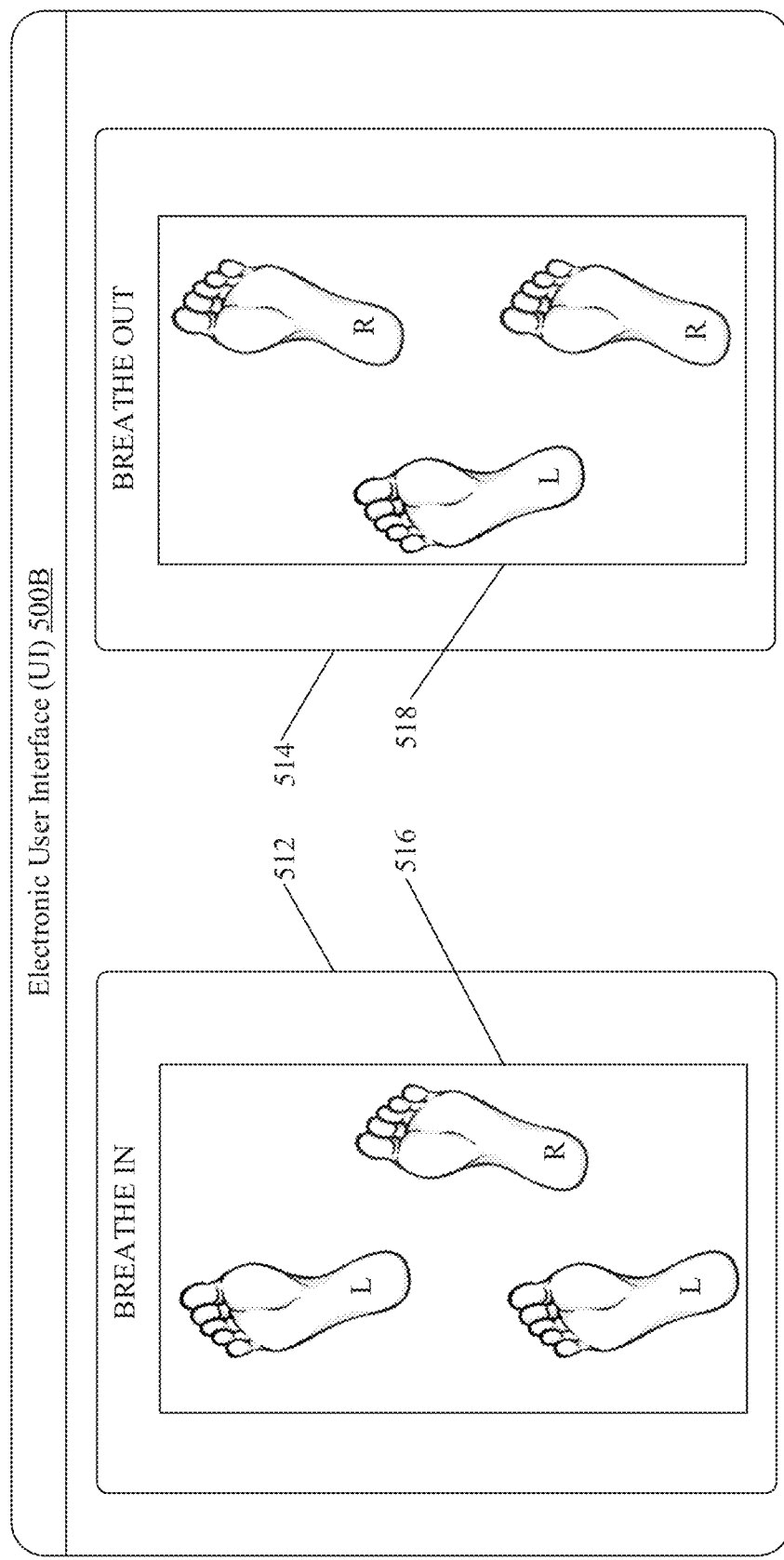
FIG. 5B is a diagram that illustrates an example electronic user interface for rendering of presentation data generated in FIG. 5A, according to at least one embodiment described in the present disclosure.

FIG. 5B is a diagram that illustrates an example electronic user interface for rendering of presentation data generated in FIG. 5A, according to at least one embodiment described in the present disclosure. FIG. 5B is explained in conjunction with elements from FIG. 1, FIG. 2, FIG. 3A, FIG. 3B, FIG. 4A, FIG. 4B, and FIG. 5A. With reference to FIG. 5B, there is shown an electronic UI 500B. The electronic UI 500B may be displayed on the display device 106. The electronic UI 500B may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

On the electronic UI 500B, there is shown a set of UI elements, such as a first UI element 512 and a second UI element 514. On the first UI element 512, a first image 516 may be displayed. Similarly, on the second UI element 514, a second image 518 may be displayed. The first image 516 and the second image 518 may collectively depict the breathing pattern 508 of the user 112 and may be referred to as an improvement suggestion in relation to a running activity (i.e. a physical activity). Such a suggestion may be included in the presentation data (generated in FIG. 5A).

The first image 516 may include an improvement suggestion (or a tip) to breathe-in by inhaling three (3) times and landing both feet according to a pattern illustrated in the first image 516. The second image 518 may include an improvement suggestion (or a tip) to breathe-out by exhaling three (3) times and landing both feet according to a pattern illustrated in the second image 518. As shown, the pattern may be to inhale three times while the landing of the left foot, right foot, and the left root. On the next landing of the right foot, the left foot, and the right foot, the user 112 may be suggested to exhale out so that a three inhalation-three exhalation breathing pattern is maintained.

Figure 5C:
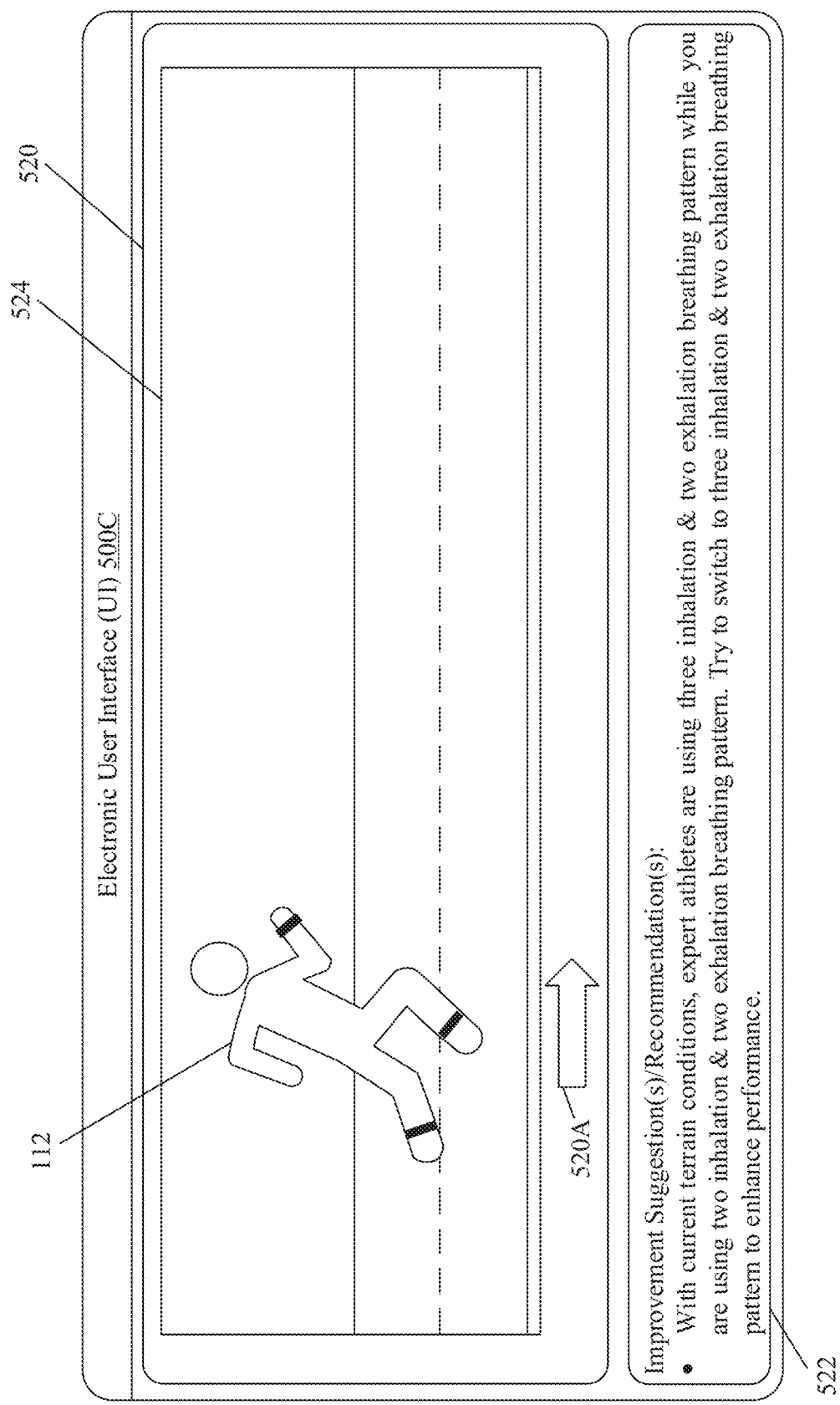
FIG. 5C is a diagram that illustrates an example electronic user interface for rendering of presentation data generated in FIG. 5A, according to at least one embodiment described in the present disclosure.

FIG. 5C is a diagram that illustrates an example electronic user interface for rendering of presentation data generated in FIG. 5A, according to at least one embodiment described in the present disclosure. FIG. 5C is explained in conjunction with elements from FIG. 1, FIG. 2, FIG. 3A, FIG. 3B, FIG. 4A, FIG. 4B, FIG. 5A, and FIG. 5B. With reference to FIG. 5C, there is shown an electronic UI 500C. The electronic UI 500C may be displayed on the display device 106. The electronic UI 500C may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

On the electronic UI 500C, there is shown a set of UI elements, such as a third UI element 520 and a fourth UI element 522. On the third UI element 520, a third image 524 of the user 112 performing the physical activity may be displayed. There is further shown fifth UI element 520A that may indicate a direction in which the user 112 may be running (i.e. a physical activity).

The fourth UI element 522 may display the one or more improvement suggestions/recommendation(s) for the user 112. As shown, for example, the suggestion may include "with current terrain conditions, expert athletes are using three inhalation and two exhalation breathing pattern while you are using two inhalation and two exhalation breathing pattern. Try to switch to three inhalation & two exhalation breathing pattern to enhance the performance". The one or more improvement suggestions/recommendation(s), if followed by the user 112, may enhance the performance of the user 112 in the physical activity. In another embodiment, a sixth UI element may be rendered on the electronic UI 500C that may display the determined one or more injuries (likely to be caused by the movement pattern or the performance in the physical activity) and recommendations to avoid the determined one or more injuries.

Figure 6:
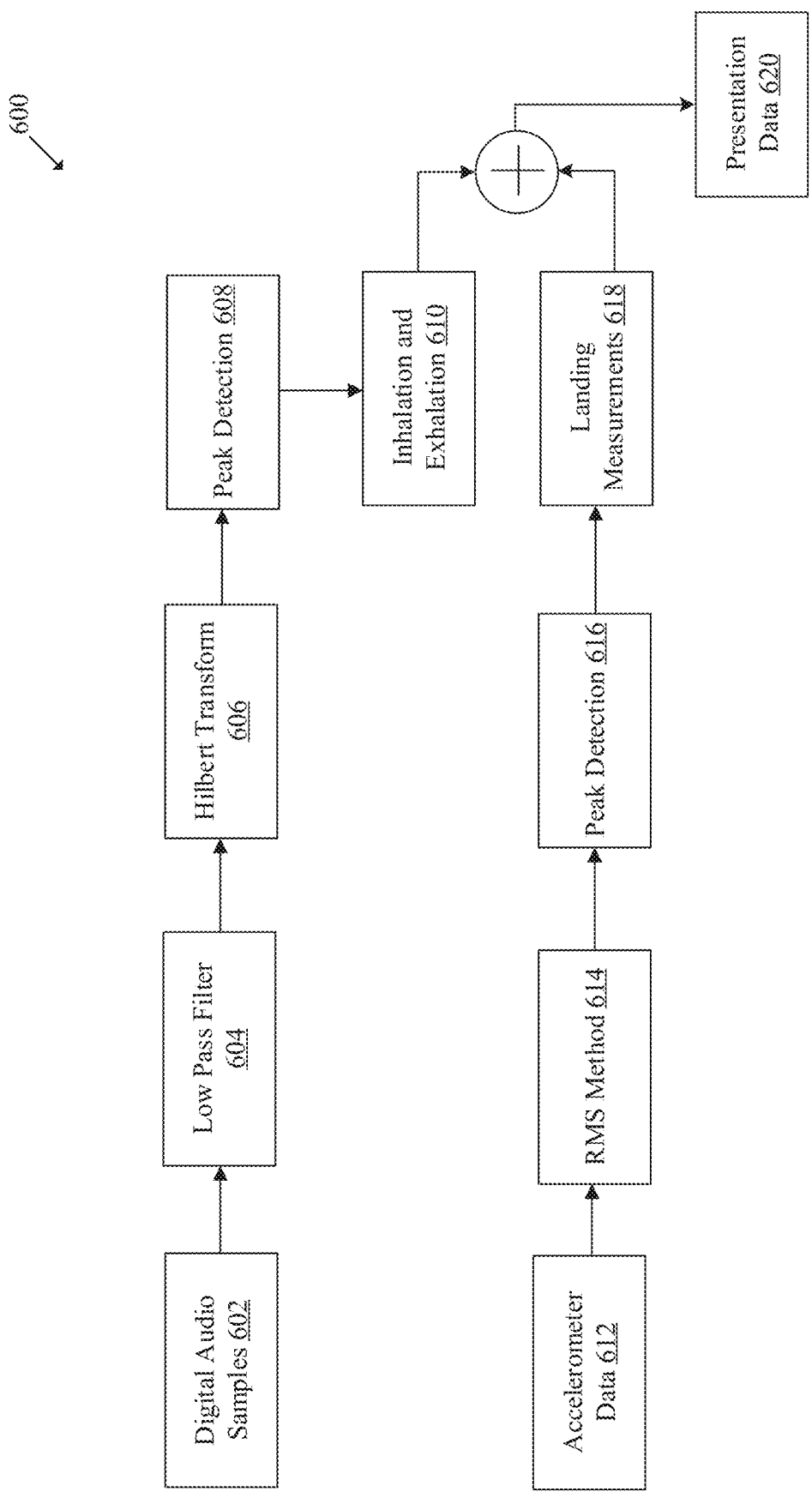
FIG. 6 is a diagram that illustrates exemplary operations for breathing data detection and foot landing measurements, in accordance with an embodiment of the disclosure.

FIG. 6 is a diagram that illustrates exemplary operations for breathing data detection and foot landing measurements, in accordance with an embodiment of the disclosure. FIG. 6 is explained in conjunction with elements from FIG. 1, FIG. 2, FIG. 3A, FIG. 3B, FIG. 4A, FIG. 4B, FIG. 5A, FIG. 5B, and FIG. 5C. With reference to FIG. 6, there is shown a block diagram 600 that includes exemplary operations for breathing data detection and foot landing measurements. The exemplary operations illustrated in the block diagram 600 may be performed by any computing system, apparatus, or device, such as by the electronic device 102 of FIG. 1 or the circuitry 202 of FIG. 2. Although illustrated with discrete blocks, the exemplary operations associated with one or more blocks of the block diagram 600A may be divided into additional blocks, combined into fewer blocks, or eliminated, depending on the particular implementation.

In operation, a breathing rate sensor worn by the user 112 may capture digital audio samples 602 of a breathing sound produced by the user 112 while performing a physical activity, such as a running activity. Multiple instances of both inspiration and expiration may be captured in the digital audio samples 602 and may be transferred in the form of the breathing data (such as the breathing data 504) to the electronic device 102. The electronic device 102 may be configured to receive the breathing data. The breathing data 504 may correspond to a duration in which the user 112 performed the physical activity. After reception, the digital audio samples 602 may be provided as an input to a low pass filter 604 to filter the digital audio samples 602 by removal of noise from the digital audio samples 602.

The circuitry 202 may apply a Hilbert transform 606 on the filtered audio samples to obtain transformed samples. Thereafter, the circuitry 202 may execute a peak detection operation 608 to detect peak(s) of the obtained samples. Based on the detected peak(s), the circuitry 202 may detect instances of inhalation and exhalation 610, which may be referred to as the breath detection data. As described in FIG. 4A, the breath detection data may be used to generate presentation data (includes improvement suggestions) in relation to a rhythmic breathing pattern.

In an embodiment, an accelerometer sensor worn by the user 112 may capture accelerometer data 612 of the foot portion of the user 112. The accelerometer data 612 may correspond to the same duration in which the user 112 performed the physical activity. The circuitry 202 may apply an RMS method 614 on the accelerometer data 612 to calculate RMS values of acceleration. Thereafter, the circuitry 202 may apply a peak detection method 616 to detect peak(s) (i.e. peak values) of the accelerometer data 612. Based on the detected peak(s) and the RMS values, the circuitry 202 may determine landing measurements 618 for both the left foot and the right foot. The landing measurements 618 may be used together with the breath detection data (or may be used independently) to generate presentation data 620 (which includes improvement suggestions) in relation to foot landing and rhythmic breathing. Examples of the presentation data 620 are described in FIGS. 4B, 5B, and 5C, for example.

Figure 7A:
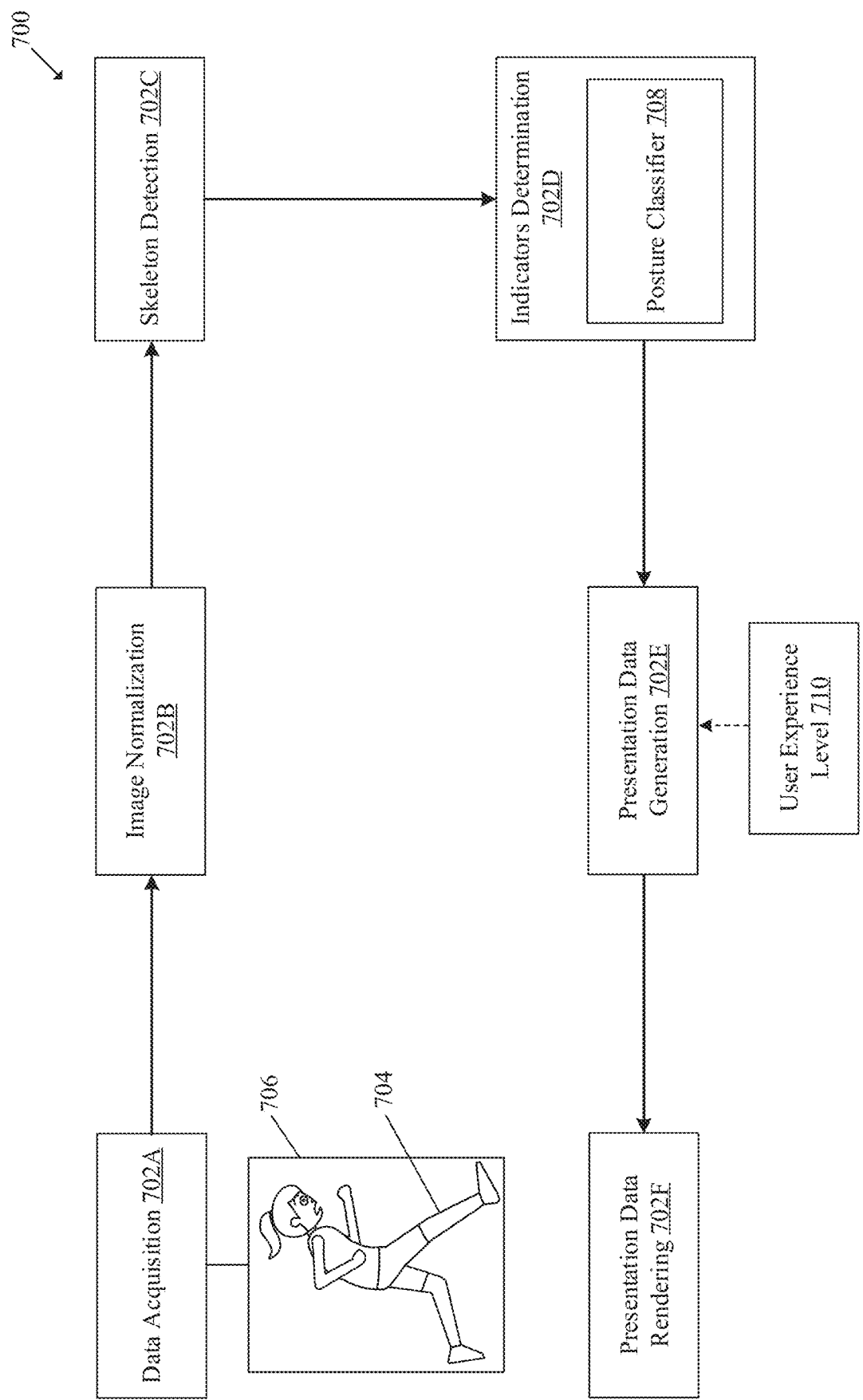
FIG. 7A is a diagram that illustrates exemplary operations for data-driven assistance for users involved in physical activities based on a posture of the user, in accordance with an embodiment of the disclosure.

FIG. 7A is a diagram that illustrates exemplary operations for data-driven assistance for users involved in physical activities based on a posture of the user, in accordance with an embodiment of the disclosure. FIG. 7A is explained in conjunction with elements from FIG. 1, FIG. 2, FIG. 3A, FIG. 3B, FIG. 4A, FIG. 4B, FIG. 5A, FIG. 5B FIGS. 5C, and 6. With reference to FIG. 7A, there is shown a block diagram 700A that illustrates exemplary operations from 702A to 702F, as described herein. The exemplary operations illustrated in the block diagram 700A may start at 702A and may be performed by any computing system, apparatus, or device, such as by the electronic device 102 of FIG. 1 or circuitry 202 of FIG. 2. Although illustrated with discrete blocks, the exemplary operations associated with one or more blocks of the block diagram 700A may be divided into additional blocks, combined into fewer blocks, or eliminated, depending on the particular implementation.

At 702A, a data acquisition operation may be performed. In the data acquisition operation, the circuitry 202 may be configured to control a set of image sensors to capture a set of images of the user 704. The set of images may be captured within the duration in which the user 704 performs the physical activity. For example, the set of images may be captured while the user 704 performs a running or sprinting activity for a duration of 10 minutes.

In an embodiment, each of the set of image sensors may be installed at the location where the user 704 performs the physical activity. Examples of such image sensors may include, but are not limited to, an action camera, an image sensor, a wide-angle camera, a closed-circuit television (CCTV) camera, a camcorder, a digital camera, camera phones, a time-of-flight camera (ToF camera), a night-vision camera, and/or other image capture devices. The set of image sensors may be further configured to transmit the captured set of images of the user 704 to the electronic device 102.

At 702B, an image normalization operation may be performed. In the image normalization operation, the circuitry 202 may be configured to normalize at least a first image 706 of the received set of images of the user 704. The first image 706 may be normalized to modify a range of pixel intensity values of the first image 706 of the user 704. The detailed implementation of the image normalization techniques may be known to one skilled in the art, and therefore, a detailed description for the image normalization technique has been omitted from the disclosure for the sake of brevity.

At 702C, a skeleton detection operation may be performed. In the skeleton detection operation, the circuitry 202 may be configured to determine skeletal joints of the user 704 in at least one of the captured (or normalized) set of images. The circuitry 202 may be also configured to detect and locate key points, such as the top of the head, neck, shoulders, elbows, wrists, hips, knees, and ankles of the body of the user 704. The key points may correspond to the skeletal joints of the user 704.

At 702D, one or more third indicators may be determined. Such indicators may be likely to have affected the user 704 (in terms of fitness level, for example) or the performance of the user 704 in the physical activity The circuitry 202 may be configured to apply a posture classifier 708 on the skeletal joints (determined at 602C) to determine the one or more third indicators. The one or more third indicators may include a first body posture of the user 704. In an embodiment, the posture classifier may be a machine learning model that may be pre-trained to process the skeletal joints (and/or the key points) to determine the first body posture of the user 704. The posture in a physical activity may be an important indicator of an experience level of the user 704, a fitness level or a form of the user 704, and the performance. Additionally, the posture may be related to performance-related factors, such as an average speed or a maximum speed at which the user 704 runs, a cadence, a symmetric load distribution on left and right foot, a low ground contact time, and a relative position of body's center of mass with respect to both the left and right foot.

In an embodiment, one or more sensors may be placed on various body parts of the user 704. The circuitry 202 may be configured to estimate the first body posture of the user 704 based on sensor data collected from the one or more sensors. By way of example and not limitation, the one or more sensors may be placed on the skeletal joints of the user 704. Each sensor may capture its corresponding position with respect to a reference frame (such as ground) as the sensor data. The circuitry may collect the sensor data and estimate the first body posture of the user 704.

At 702E, a presentation data generation operation may be performed. In the presentation data generation operation, the circuitry 202 may be configured to generate the presentation data based on application of the first ML model 104 on the determined one or more third indicators. The generated presentation data may include one or more improvement suggestions associated with the first body posture. Specifically, the one or more improvement suggestions may include instructions to correct the first body posture while performing the physical activity. For example, an improvement suggestion may prompt the user 704 to have the arms tight and to keep a forward posture with the feet always falling under (or almost) the body's center of mass. An example of the presentation data is provided, for example, in FIG. 7B.

In an embodiment, the generated presentation data may include a comparison of the first body posture of the user 704 with that of an expert athlete. For such comparison, the circuitry 202 may determine a user experience level 710 in the physical activity. The user experience level 710 may be used for comparison of the performance or specific performance-indicators of the user 704 with that of an expert athlete. In an embodiment, to determine the user experience level 710, the circuitry 202 may be configured to apply the second ML model 210 on the determined one or more third indicators and/or the first information (about the location) to generate a classification result. The classification result may include one or more labels that identify the user 112 as one of an amateur athlete, an intermediate or average athlete, or an expert athlete. The circuitry 202 may be configured to determine the user experience level 710 in relation to the physical activity, based on the classification result.

At 702F, a presentation data rendering operation may be performed. In the presentation data rendering operation, the circuitry 202 may be configured to control the display device 106 to display the generated presentation data. In an embodiment, the presentation data may be displayed on an electronic user Interface (UI) that may be rendered on a display screen of the display device 106, as described in FIG. 7B.

Figure 7B:
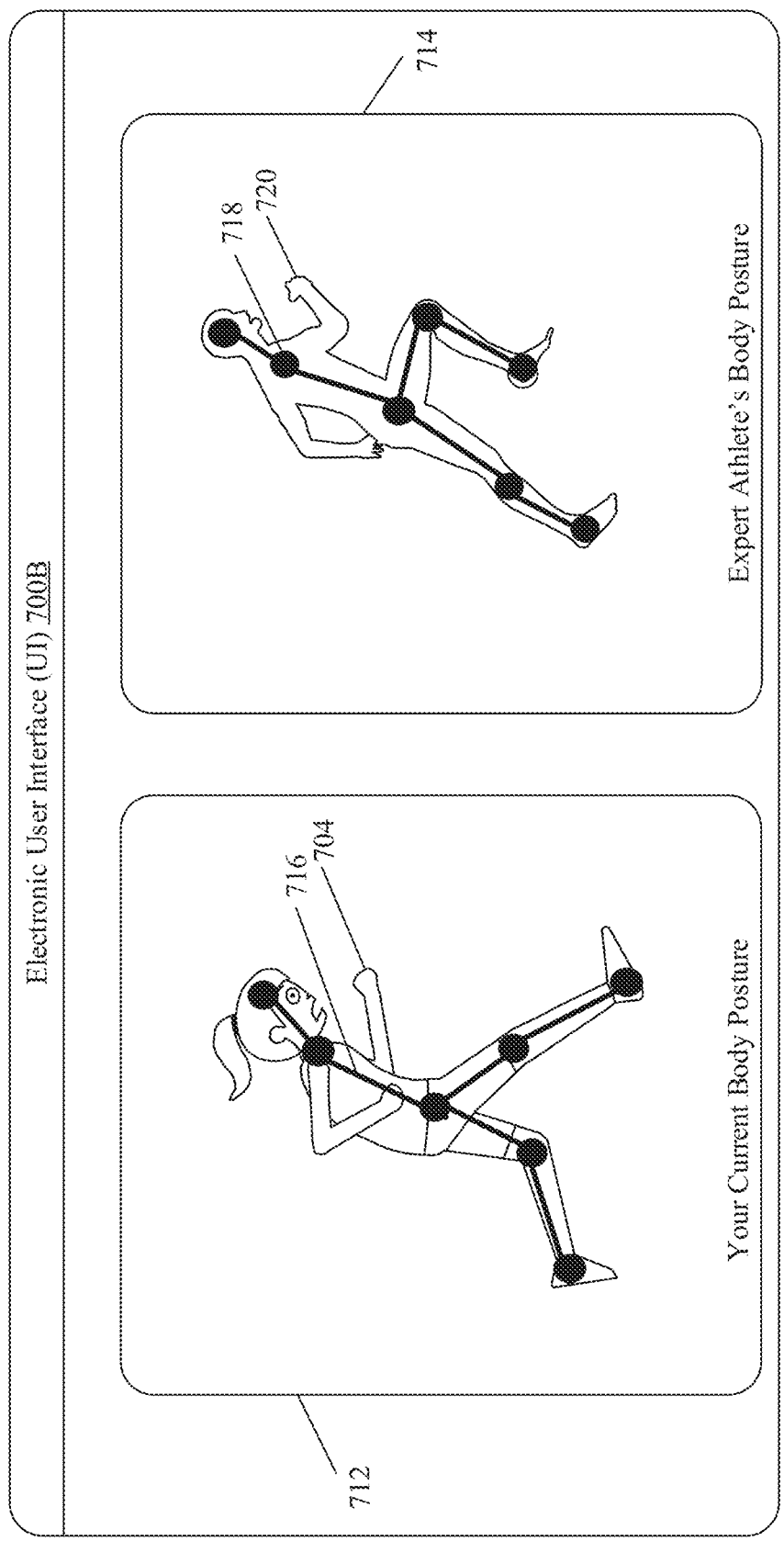
FIG. 7B is a diagram that illustrates an example electronic user interface for rendering of presentation data generated in FIG. 7A, according to at least one embodiment described in the present disclosure.

FIG. 7B is a diagram that illustrates an example electronic user interface for rendering of presentation data generated in FIG. 7A, according to at least one embodiment described in the present disclosure. FIG. 7B is explained in conjunction with elements from FIG. 1, FIG. 2, FIG. 3A, FIG. 3B, FIG. 4A, FIG. 4B, FIG. 5A, FIG. 5B, FIG. 5C, FIG. 6, and FIG. 7A. With reference to FIG. 7B, there is shown an electronic UI 700B. The electronic UI 700B may be displayed on the display device 106. The electronic UI 700B may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

On the electronic UI 700B, there is shown a set of UI elements, such as a first UI element 712 and a second UI element 714. On the first UI element 712, a first body posture 716 of the user 704 may be displayed. On the second UI element 714, a body posture 718 of an expert athlete 720 may be displayed. The body posture 718 may be displayed as part of an improvement suggestion for the user 704. The user 704 may be able to compare his/her own body posture (i.e. the first body posture 716) with the body posture 718 of the expert athlete 720. The first body posture 716, if corrected in accordance to the body posture 718, may increase the performance of the user 704 in the physical activity. In another embodiment, the one or more improvement suggestions for the correction of the first body posture 716 may be displayed on a third UI element (not shown). In another embodiment, one or more injuries, likely to be caused by the first body posture 716 may be displayed along with the recommendations to avoid such injuries.

Figure 8:
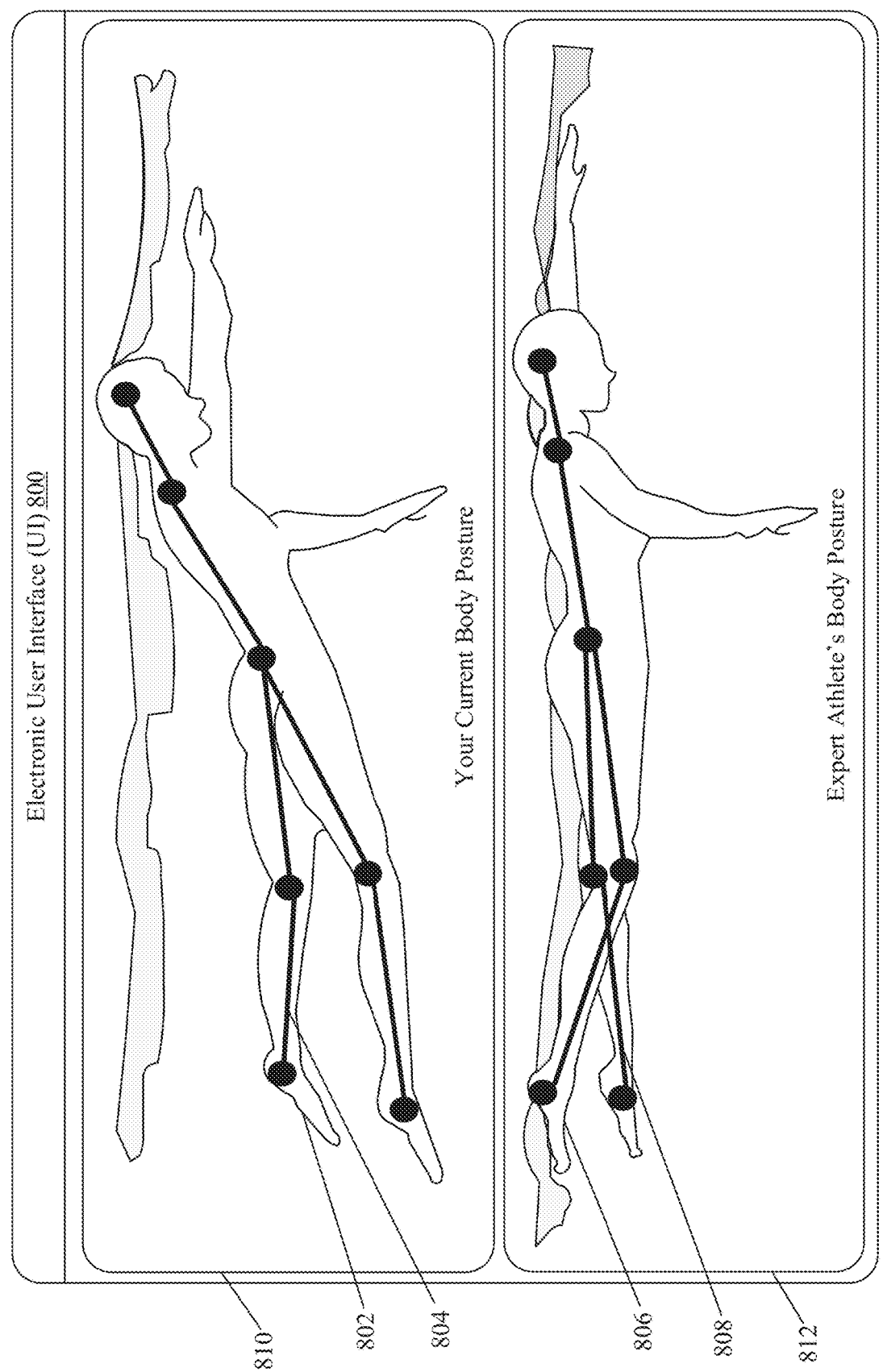
FIG. 8 is a diagram that illustrates an example electronic user interface for rendering of presentation data associated with swimming activity, according to at least one embodiment described in the present disclosure.

FIG. 8 is a diagram that illustrates an example electronic user interface for rendering of presentation data associated with a swimming activity, according to at least one embodiment described in the present disclosure. FIG. 8 is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, and FIG. 7B. With reference to FIG. 8, there is shown an electronic UI 800. The electronic UI 800 may be displayed on the display device 106. The electronic UI 800 may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

The circuitry 202 may be configured to receive first sensor data, associated with a movement pattern of the one or more parts of a body of a user 802, for the duration of in which the user 802 is swimming. Specifically, the circuitry 202 may be configured to control the set of image sensors to capture a first set of images of the user 802. The first set of images may be captured within a duration in which the user 802 performs the physical activity. For example, the first set of images may be captured while the user 802 performs swimming activity for a duration of 5 minutes.

In an embodiment, each of the first set of image sensors may be installed at the location where the user 802 performs the physical activity. Examples of such image sensors may include, but are not limited to, an action camera, an image sensor, a wide-angle camera, a closed-circuit television (CCTV) camera, a camcorder, a digital camera, camera phones, a time-of-flight camera (ToF camera), a night-vision camera, and/or other image capture devices. The first set of image sensors may be further configured to transmit the captured set of images of the user 802 to the electronic device 102.

In an embodiment, the circuitry 202 may be configured to normalize at least a first image of the received first set of images of the user 802. The first image may be normalized to modify a range of pixel intensity values of the first image of the user 802. The detailed implementation of the image normalization techniques may be known to one skilled in the art, and therefore, a detailed description for the image normalization technique has been omitted from the disclosure for the sake of brevity.

The circuitry 202 may be configured to determine locations of skeletal joints of the user 802 in at least one of the captured (or normalized) first set of images. As discussed in FIG. 7A, the circuitry 202 may be also configured to detect and locate key points, such as the top of the head, neck, shoulders, elbows, wrists, hips, knees, and ankles of the body. The key points may correspond to the locations of the skeletal joints of the user 802.

The circuitry 202 may be configured to determine one or more fourth indicators. Such indicators may be likely to have affected the user 802 or the performance of the user 802 in swimming. The circuitry 202 may apply the posture classifier 708 on the determined skeletal joints to determine the one or more fourth indicators. The one or more fourth indicators may include a first body posture 804 of the user 802. As already discussed, the posture classifier 708 may be a machine learning model that may be pre-trained to process the skeletal joints (and/or the key points) to determine the first body posture 804 of the user 802. The posture in swimming may be an important indicator of an experience level of the user 802, a fitness level or a form of the user 802, and the performance.

Based on the determined one or more fourth indicators, the circuitry 202 may be configured to generate the presentation data based on application of the first ML model 104 on the determined one or more fourth indicators. The generated presentation data may include one or more improvement suggestions associated with the first body posture 804 of the user 802. Specifically, the one or more improvement suggestions may include instructions to correct the first body posture 804 during swimming. For example, an improvement suggestion may include a prompt to the user 802 to not to tilt the body in water because it increases resistance, to keep the body parallel to the waterline, and to keep the head down.

In an embodiment, the generated presentation data may include a comparison of the first body posture 804 of the user 802 with that of an expert athlete 806. For such comparison, the circuitry 202 may determine a user experience level in the swimming. The user experience level may be used for comparison of the performance or specific performance-indicators of the user 802 with a second body posture 808 of an expert athlete 806. In an embodiment, to determine the user experience level, the circuitry 202 may be configured to apply the second ML model 210 on the determined one or more fourth indicators to generate a classification result. The classification result may include one or more labels that identify the user 802 as one of an amateur athlete, an intermediate or average athlete, or an expert athlete. The circuitry 202 may be configured to determine the user experience level in relation to swimming, based on the classification result.

The circuitry 202 may be further configured to render the generated presentation data. Specifically, the circuitry 202 may be configured to control the display device 106 to display the generated presentation data. An example of the presentation data for swimming activity is provided herein.

With reference to FIG. 8, there is shown an electronic user Interface (UI) 800 that may be rendered on a display screen of the display device 106. On the electronic UI 800, there is shown a set of UI elements, such as a first UI element 810 and a second UI element 812. On the first UI element 810, a first body posture 804 of the user 802 may be displayed. On the second UI element 812, the second body posture 808 of an expert athlete 806 may be displayed. The body posture may be displayed as part of an improvement suggestion for the user 802. The user 802 may be able to compare his/her own body posture (i.e. the first body posture 804) with the second body posture 808 of the expert athlete 806. The first body posture 804, if corrected in accordance to the second body posture 808 of the expert athlete 806, may increase the performance of the user 802 in the physical activity. In another embodiment, the one or more improvement suggestions for the correction of the first body posture 804 may be displayed on a third UI element (not shown). In another embodiment, one or more injuries, likely to be caused by the first body posture 804 may be displayed along with the recommendations to avoid such injuries.

Figure 9A:
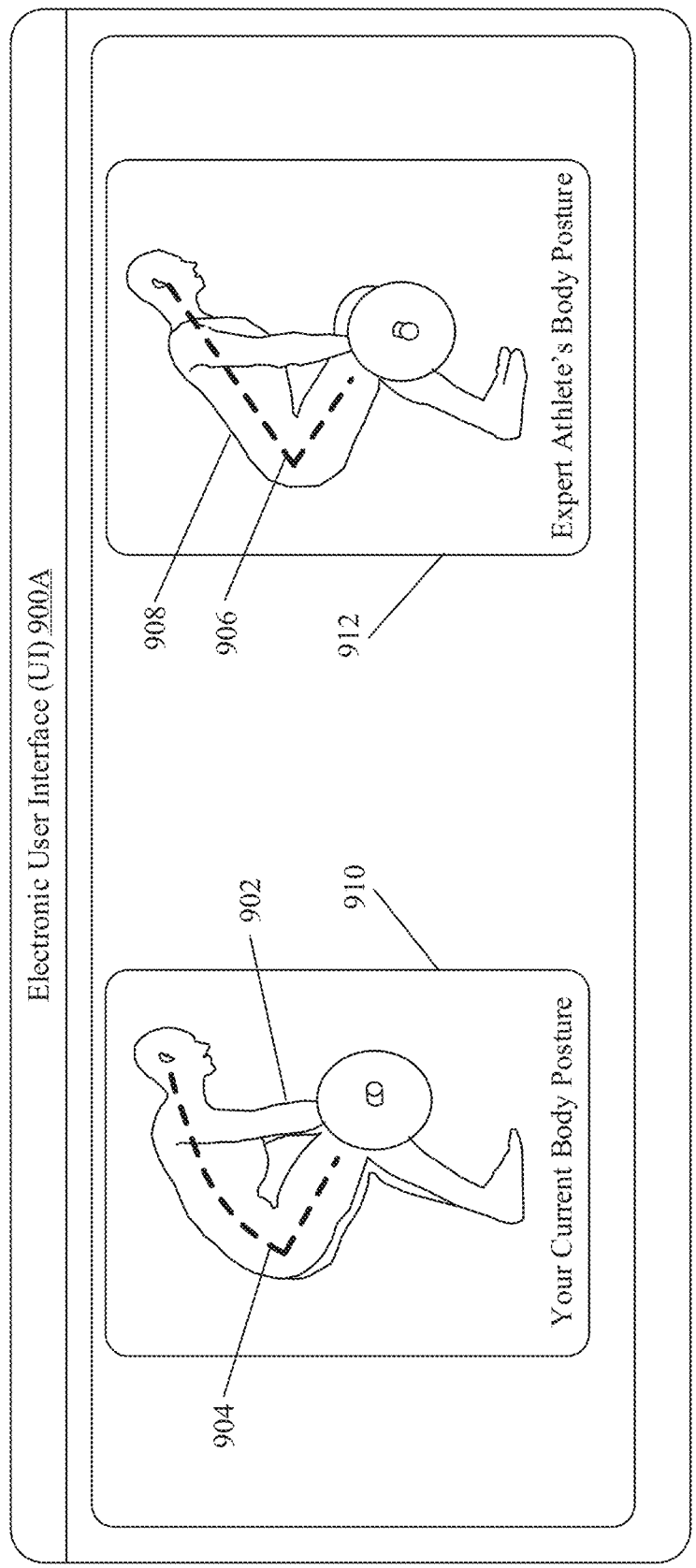
FIG. 9A is a diagram that illustrates an example electronic user interface for rendering of presentation data associated with deadlifting, according to at least one embodiment described in the present disclosure.

FIG. 9A is a diagram that illustrates an example electronic user interface for rendering of presentation data associated with deadlifting, according to at least one embodiment described in the present disclosure. FIG. 9A is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, FIG. 7B, and FIG. 8. With reference to FIG. 9A, there is shown an electronic UI 900A. The electronic UI 900A may be displayed on the display device 106. The electronic UI 900A may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

The circuitry 202 may be configured to receive first sensor data, associated with a movement pattern of the one or more parts of a body of a user 902, for the duration of in which the user 902 is a deadlifting activity. Specifically, the circuitry 202 may be configured to control the set of image sensors to capture a second set of images of the user 902.

The circuitry 202 may determine one or more fifth indicators based on the captured second set of images of the user 902. Such indicators may be likely to have affected the user 902 or the performance of the user 902 in the deadlifting activity. In an embodiment, the circuitry 202 may apply the posture classifier 708 on one or more skeletal joints of the user 902 to determine the one or more fifth indicators. The one or more fifth indicators may include a body posture 904 of the user 902. As already discussed, the posture classifier 708 may be a machine learning model that may be pre-trained to process the skeletal joints (and/or the key points) to determine the body posture 904 of the user 902. The posture in deadlifting may be an important indicator of an experience level of the user 902, a fitness level or a form of the user 902, and the performance.

Based on the determined one or more fifth indicators, the circuitry 202 may be configured to generate presentation data based on application of the first ML model 104 on the determined one or more fifth indicators. The generated presentation data may include one or more improvement suggestions associated with the body posture 904 of the user 902. Specifically, the one or more improvement suggestions may include instructions to correct the body posture 904 while performing the deadlifting activity. For example, an improvement suggestion may prompt the user 902 to keep the back and head straight, to the bend a bit more so that an angle between an upper leg of the user 902 and the lower leg of the user 902 is equal to or approximately equal to 90°, and to keep the head straight.

In an embodiment, the generated presentation data may include a comparison of the body posture 904 of the user 902 with a body posture 906 an expert athlete 908. For such comparison, the circuitry 202 may determine a user experience level in the deadlifting activity. The circuitry 202 may determine one or more labels that identify the user 802 as one of an amateur athlete, an intermediate or average athlete, or an expert athlete. The user experience level may be determined in relation to the deadlifting activity, based on the determined result.

The circuitry 202 may be further configured to render the generated presentation data. Specifically, the circuitry 202 may be configured to control the display device 106 to display the generated presentation data. In an embodiment, the presentation data may be displayed on the electronic user Interface (UI) 900A that may be rendered on a display screen of the display device 106.

On the electronic UI 900A, there is shown a set of UI elements, such as a first UI element 910 and a second UI element 912. On the first UI element 910, the body posture 904 of the user 902 may be displayed. On the second UI element 912, the body posture 906 of the expert athlete 908 may be displayed. The body posture may be displayed as part of an improvement suggestion for the user 902. The user 902 may be able to compare his/her own body posture (i.e. the body posture 904) with the body posture 906 of the expert athlete 908. The body posture 904, if corrected in accordance to the body posture 906 of the expert athlete 908, may increase the performance of the user 902 in the physical activity. In another embodiment, the one or more improvement suggestions for the correction of the body posture 904 may be displayed on a third UI element (not shown). In another embodiment, one or more injuries, likely to be caused by the body posture 904 may be displayed along with the recommendations to avoid such injuries.

Figure 9B:
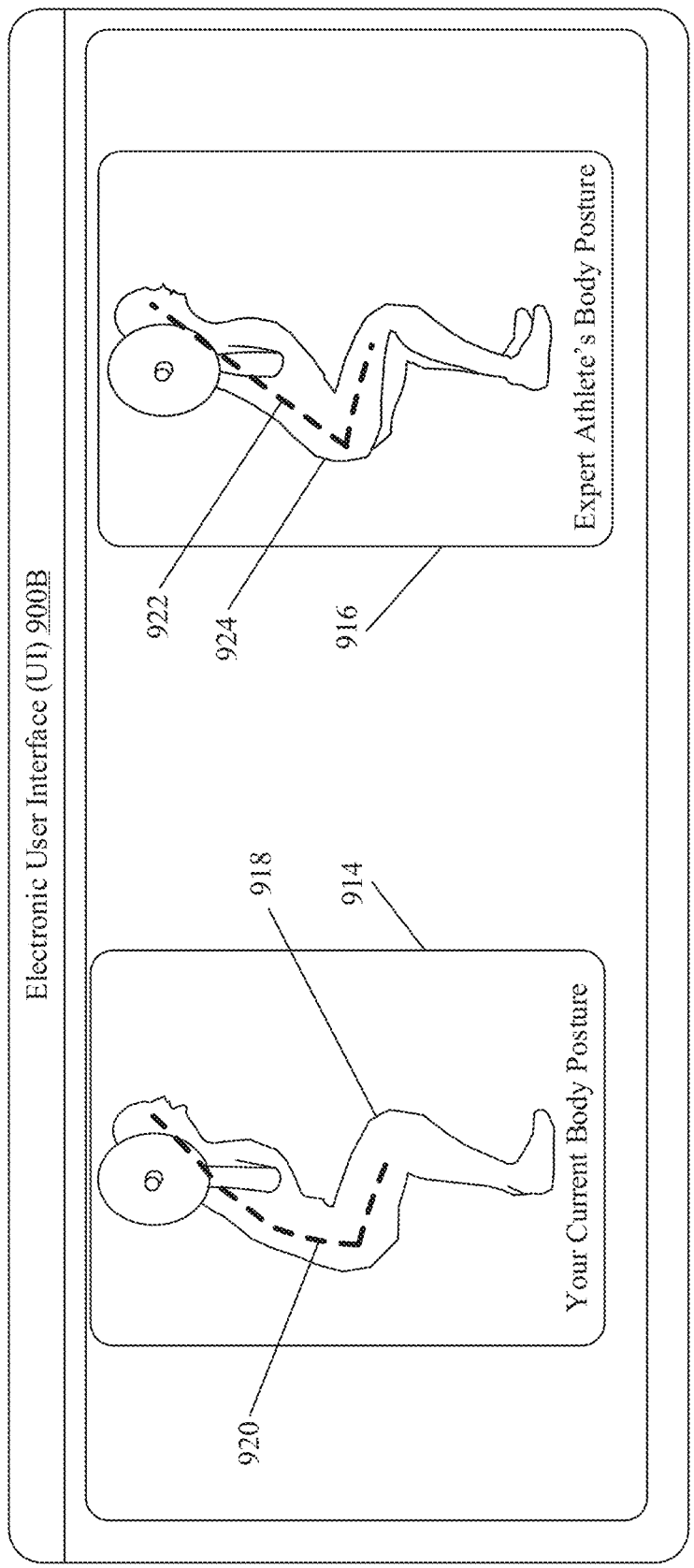
FIG. 9B is a diagram that illustrates an example electronic user interface for rendering of presentation data associated with squats, according to at least one embodiment described in the present disclosure.

FIG. 9B is a diagram that illustrates an example electronic user interface for rendering of presentation data associated with a squatting activity, according to at least one embodiment described in the present disclosure. FIG. 9B is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, FIG. 7B, FIG. 8, and FIG. 9A. With reference to FIG. 9B, there is shown an electronic UI 900B. The electronic UI 900B may be displayed on the display device 106. The electronic UI 900B may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

On the electronic UI 900B, there is shown a set of UI elements, such as a first UI element 914 and a second UI element 916. On the first UI element 914, a body posture 918 of a user 920 may be displayed. On the second UI element 916, a body posture 922 of an expert athlete 924 may be displayed. The body posture may be displayed as part of an improvement suggestion for the user 920. The user 920 may be able to compare his/her own body posture (i.e. the body posture 918) with the body posture 922 of the expert athlete 924. The body posture 918, if corrected in accordance to the body posture 922 of the expert athlete 924, may increase the performance of the user 902 in the squats. In another embodiment, the one or more improvement suggestions for the correction of the body posture 918 may be displayed on a third UI element (not shown). In another embodiment, one or more injuries, likely to be caused by the body posture 918 may be displayed along with the recommendations to avoid such injuries.

Figure 10:
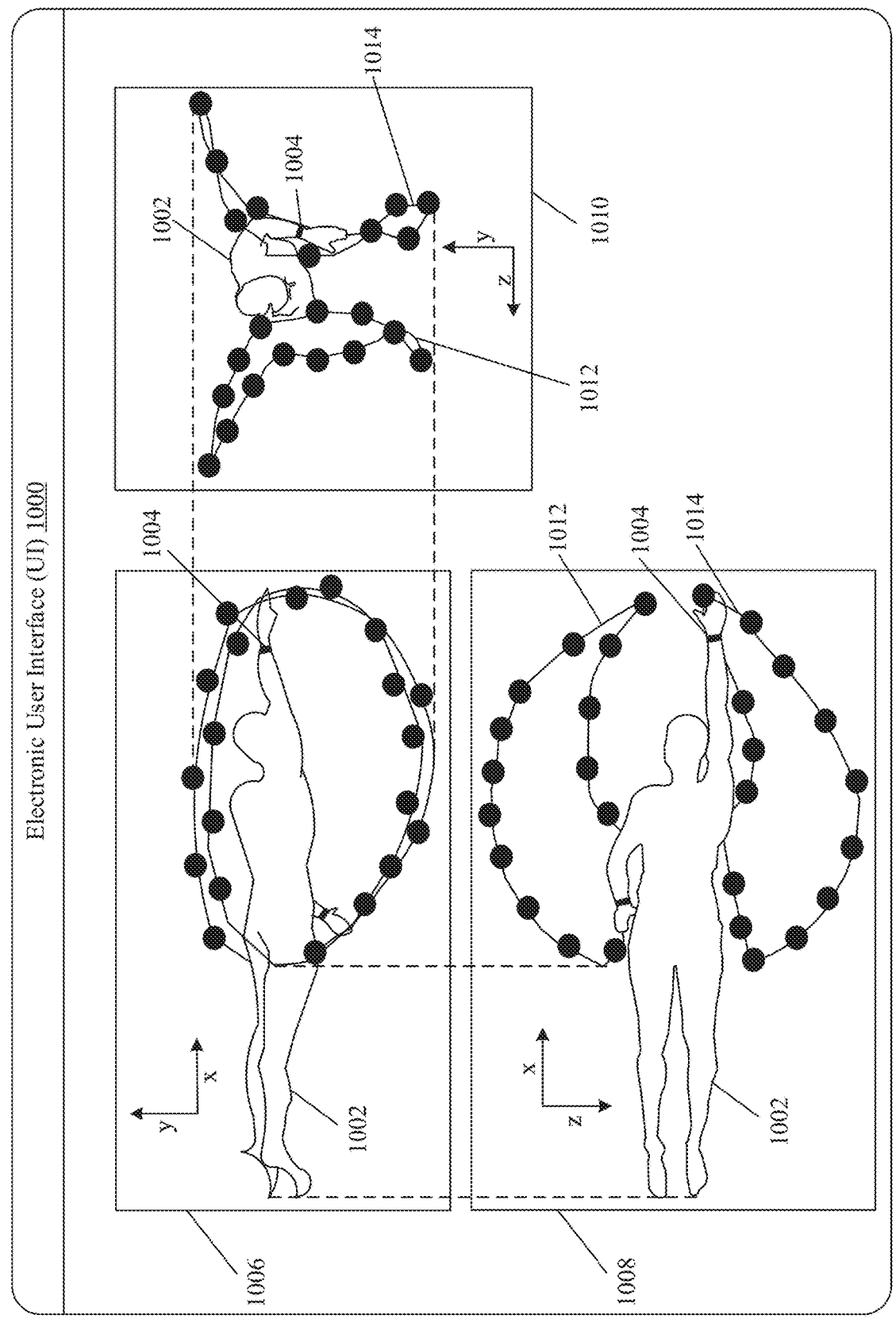
FIG. 10 is a diagram that illustrates an example electronic user interface for rendering of recommendations for improvement in swimming, according to at least one embodiment described in the present disclosure.

FIG. 10 is a diagram that illustrates an example electronic user interface for rendering of recommendations for improvement in a swimming activity, according to at least one embodiment described in the present disclosure. FIG. 10 is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, FIG. 7B, FIG. 8, FIG. 9A, and FIG. 9B. With reference to FIG. 10, there is shown an electronic UI 1000. The electronic UI 1000 may be displayed on the display device 106. The electronic UI 1000 may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

The circuitry 202 may be configured to receive first sensor data associated with a movement pattern of arms of a user 1002. The first sensor data may correspond to a duration in which the user 1002 performs a swimming activity. In some embodiments, the circuitry 202 may be configured to receive the first sensor data from one or more sensors. In an embodiment, the one or more sensors may be worn by the user 112, while the user 1002 may be swimming. For example, the user 1002 may wear a first sensor 1004 on the arms. The first sensor 1004 may be configured to capture data indicative of the movement pattern of the arms of the user 1002. In another embodiment, the one or more sensors may correspond to a set of image sensors that may capture a set of images of the user 1002. The set of images may be captured within the duration in which the user 1002 may perform the swimming activity.

With reference to FIG. 10, there is further shown a first image 1006, a second image 1008, and a third image 1010 of the captured set of images of the user 1002 from different viewpoints. For example, the first image 1006 may be a side view of the user 1002 while swimming, the second image 1008 may be a top view of the user 1002 while swimming, and the third image 1010 may be a front view of the user 1002 while swimming.

The circuitry 202 may be further configured to determine one or more indicators that may be likely to have affected the performance of the user 1002 while performing the swimming activity. The circuitry 202 may be further configured to generate presentation data. The presentation data may be generated based on the application of the first ML model 104 on the determined one or more indicators. The generated presentation data may include one or more improvement suggestions for the user 1002 in relation to the movement of the arms during swimming.

In an embodiment, the one or more improvement suggestions may be based on the movement pattern of one or more expert athletes (pre-recorded while such expert athletes performed the swimming activity). The circuitry 202 may be configured to apply the second machine learning model 210 on the determined one or more indicators. Thereafter, the circuitry 202 may determine an experience level of user 1002 in relation to the swimming activity and may generate the presentation data based on the determined experience level. The circuitry 202 may be further configured to control the display device to display the presentation data.

As shown in FIG. 10, the presentation data may include a first improvement suggestion 1012 regarding a movement of the left arm of the user 1002 and a second improvement suggestion 1014 regarding the movement of the right arm of the user 1002. In some embodiments, the one or more improvement suggestions may be presented in three dimensions (3D) by using a suitable 3D graphics engine. For example, the first image 1006 may indicate a movement of the left arm and the right arm along Y and X axis, the second image 1008 may indicate a movement of the left arm and the right arm along X and Z axis, and the third image 1010 may indicate a movement of the left arm and the right arm along Z and Y axis. These details may be provided to the user 1002 so that the user 1002 clearly understands the improvement suggestions and follows such suggestions to improve his/her skills in the swimming activity.

Figure 11A:
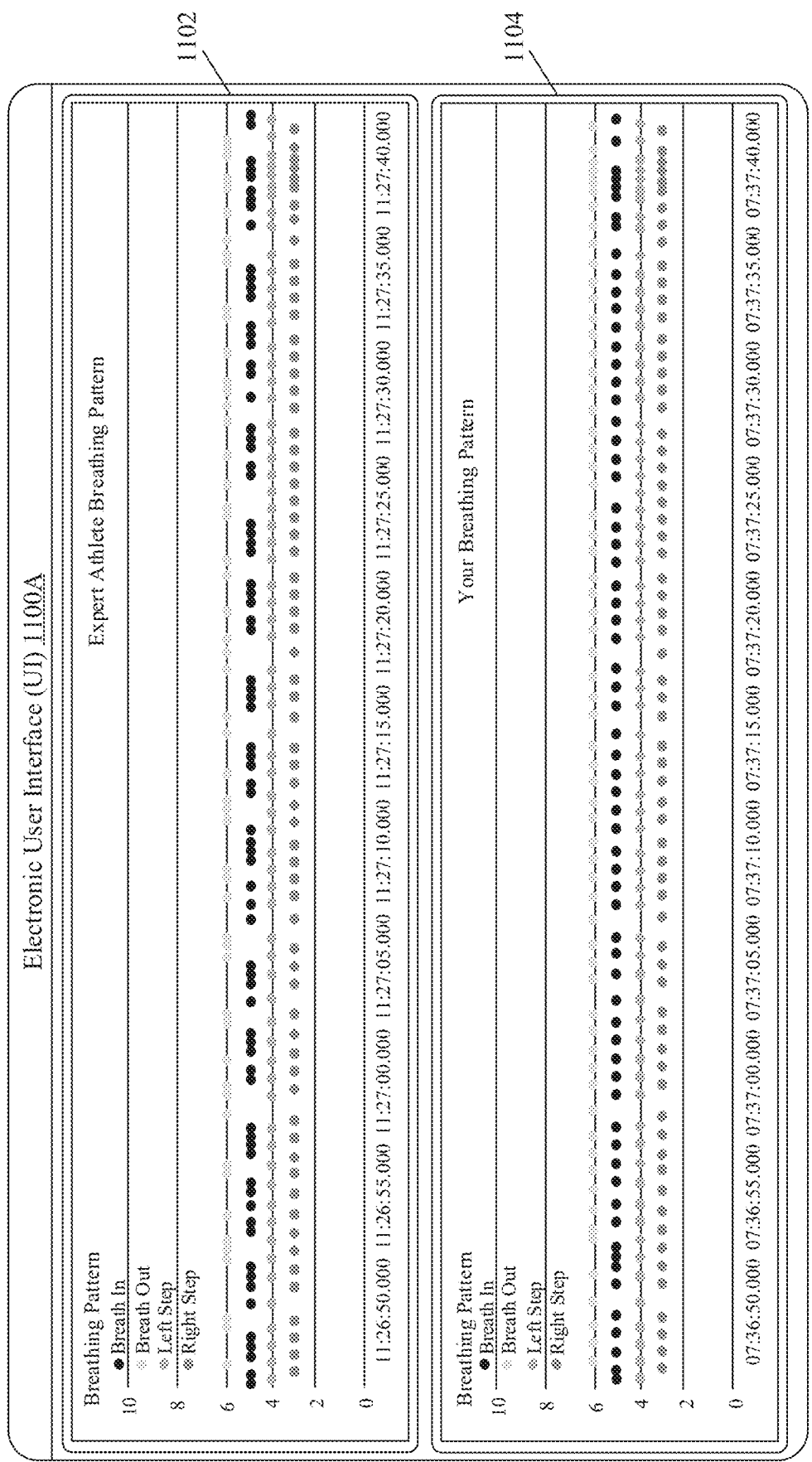
FIG. 11A is a diagram that illustrates an example electronic user interface for rendering of first visual data, according to at least one embodiment described in the present disclosure.

FIG. 11A is a diagram that illustrates an example electronic user interface for rendering of first visual data, according to at least one embodiment described in the present disclosure. FIG. 11A is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, FIG. 7B, FIG. 8, FIG. 9A, FIG. 9B, and FIG. 10. With reference to FIG. 11A, there is shown an electronic UI 1100A. The electronic UI 1100A may be displayed on the display device 106. The electronic UI 1100A may be part of an application interface displayed onto a display screen of the display device 106. The application interface may be part of an application software, for example, a software development kit (SDK), a cloud server-based application, a web-based application, an OS-based application/application suite, an enterprise application, and a mobile application.

On the electronic UI 1100A, there is shown a first UI element 1102 and a second UI element 1104. The first UI element 1102 may display a first chart representing a first breathing pattern of the expert athlete 720. The first breathing pattern may be a known indicator of the expert athlete 720 and may be recorded while the expert athlete 720 performs the physical activity at the same (or similar) location where the user 112 performs the physical activity or a different location.

The second UI element 1104 may display a second dot chart representing a second breathing pattern of the user 112. The second breathing pattern may be included in the presentation data (generated in FIG. 5A, for example). The first UI element 1102 and the second UI element 1104 may collectively be referred as the visual data included in the generated presentation data. The visual data may allow the user 112 to improve the breathing pattern by observing the breathing pattern of the expert athlete and also help the user 112 to identify one or more mistakes associated with his/her own breathing pattern.

Figure 11B:
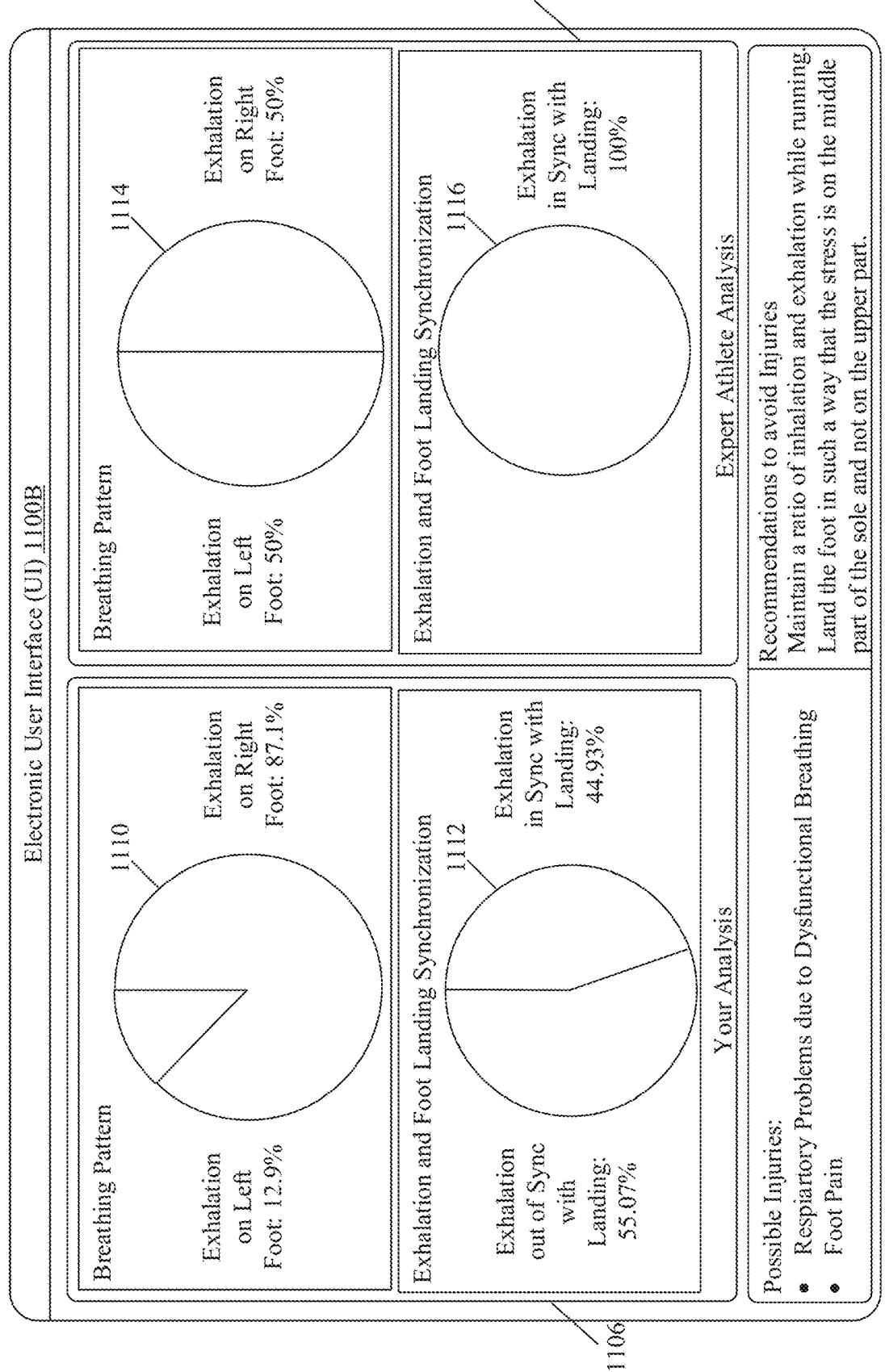
FIG. 11B is a diagram that illustrates an example electronic user interface for rendering of second visual data, according to at least one embodiment described in the present disclosure.

FIG. 11B is a diagram that illustrates an example electronic user interface for rendering of second visual data, according to at least one embodiment described in the present disclosure. FIG. 11B is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, FIG. 7B, FIG. 8, FIG. 9A, FIG. 9B, FIG. 10, and FIG. 11A. With reference to FIG. 11B, there is shown an electronic UI 1100B. The electronic UI 1100B may be displayed on the display device 106. The electronic UI 1100B may part of an application interface displayed onto a display screen of the display device 106. The application interface may be part of an application software, for example, a software development kit (SDK), a cloud server-based application, a web-based application, an OS-based application/application suite, an enterprise application, and a mobile application.

With reference to FIG. 11B, there is shown a third UI element 1106 and a fourth UI element 1108. The third UI element 1106 may display a first pie chart 1110 and a second pie chart 1112. The first pie chart 1110 may indicate a breathing pattern of the user 112 in terms of percentage (%) exhalation on landing left foot and right foot on ground. The second pie chart 1112 may indicate a percentage deviation (or out of synch) between exhalation and landing of left and right foot on ground. The second pie chart 1112 may be referred to as a chart of exhalation and foot landing synchronization.

The fourth UI element 1108 may display a third pie chart 1114 and a fourth pie chart 1116 associated with one or more indicators of an expert athlete. The third pie chart 1114 may indicate a breathing pattern of an expert athlete in terms of percentage (%) exhalation on landing left foot and right foot on ground. The fourth pie chart 1116 may indicate a percentage deviation (or out of synch) between exhalation and landing of left and right foot of the expert athlete on ground. The fourth pie chart 1116 may be referred to as a chart of exhalation and foot landing synchronization.

As shown, for example, the exhalation of the user 112 may be 87.1% on the right foot and 12.9% on the left foot. Whereas, the exhalation of the expert athlete on the right foot and the left foot may be 50%. While the expert athlete may exhale evenly on the right foot and the left foot, the user 112 may exhale more on right foot. As another example, the exhalation and foot landing of the user 112 may be inconsistent. The synchronization of the exhalation and the foot landing of the user 112 may be 44.93% only. Whereas the synchronization of the exhalation and the foot landing of the expert athlete may be 100%.

With reference to FIG. 11B, there is further shown a third UI element 1118. The third UI element 1118 may display one or more injuries, likely to be caused by the movement pattern or the performance of the user 112 in the physical activity. The third UI element 1118 may display recommendations to avoid the one or more injuries. For example, the recommendations may caution that the user 112 can face one or more respiratory problems due to dysfunctional breathing and foot pain based on the movement pattern or the performance of user 112 in the physical activity. The recommendation to avoid the injuries may be to maintain a balanced ratio (such as 1:1) of inhalation and exhalation while running and to land both the left feet and the right feet in such a way that the stress is on the middle part of the sole and not on the upper part.

Figure 12:
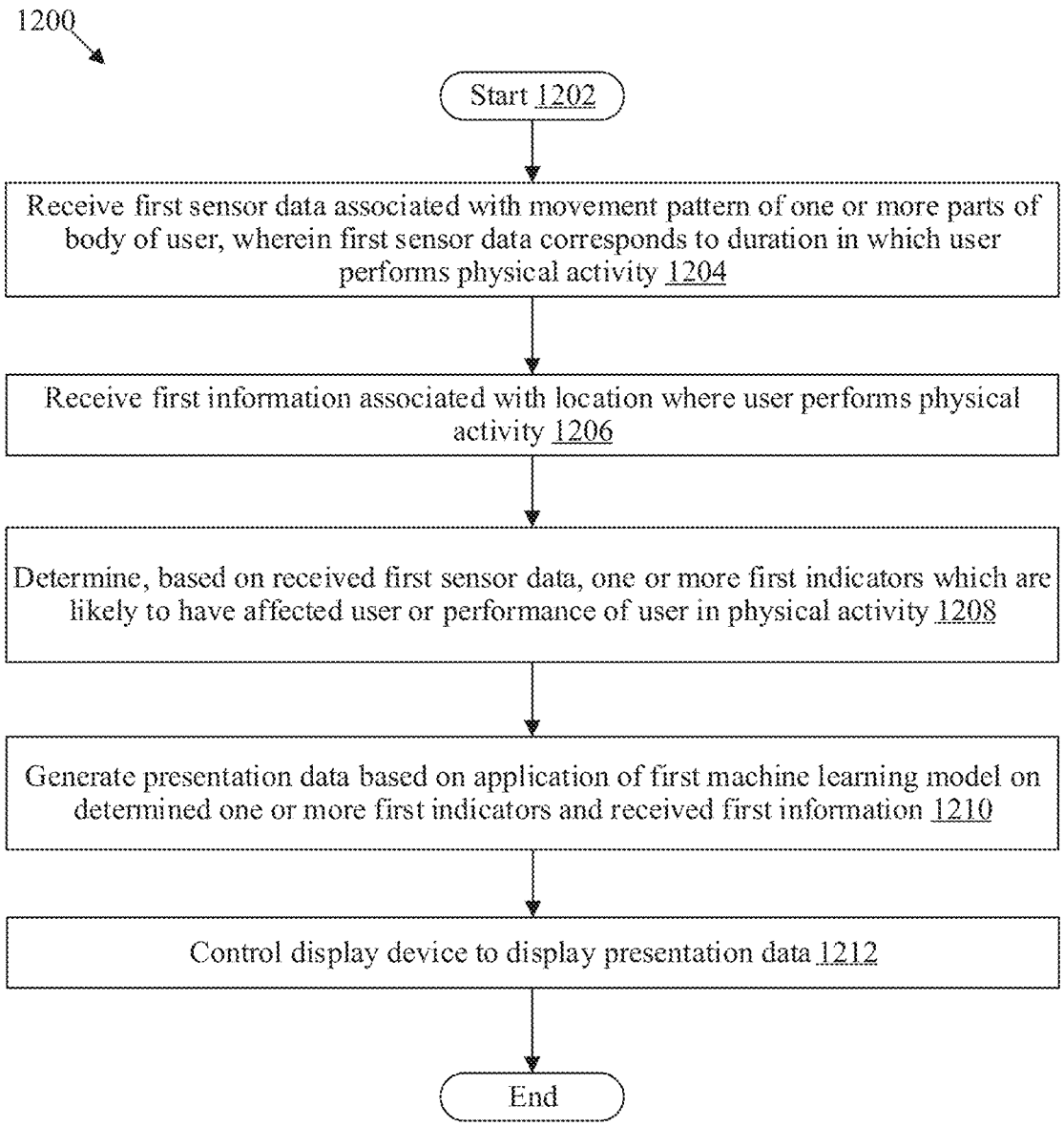
FIG. 12 is a first flowchart that illustrates exemplary operations for data-driven assistance for users involved in physical activities, in accordance with an embodiment of the disclosure.

FIG. 12 is a first flowchart that illustrates exemplary operations for data-driven assistance for users involved in physical activities, in accordance with an embodiment of the disclosure. FIG. 12 is explained in conjunction with elements from FIG. 1, FIG. 2, FIG. 3A, FIG. 3B, FIG. 4A, FIG. 4B, FIG. 5A, FIG. 5B, FIG. 5C, FIG. 6, FIG. 7A, FIG. 7B, FIG. 8, FIG. 9A, FIG. 9B, FIG. 10, FIG. 11A, and FIG. 11B. With reference to FIG. 12, there is shown a flowchart 1200. The operations from 1202 to 1212 may be implemented on any computing device, for example, the electronic device 102 or the circuitry 202. The operations may start at 1202 and proceed to 1204.

At 1204, the first sensor data 302A associated with the movement pattern of the one or more parts of the body of the user 112 may be received. The first sensor data 302A may correspond to a duration in which the user 112 performs the physical activity. In one or more embodiments, the circuitry 202 may be configured to the receive the first sensor data 302A associated with the movement pattern of the one or more parts of the body of the user 112. The details about the first sensor data 302A data are provided for example, in FIGS. 1, 3A, 4A, 5A, and 7A.

At 1206, the first information 302B associated with the location where the user 112 performs the physical activity may be received. In one or more embodiments, the circuitry 202 may be configured to receive first information 302B associated with the location where the user 112 performs the physical activity. The details about the reception of the first information are provided, for example, in FIGS. 1, 3A, 4A, 5A, and 7A.

At 1208, the one or more first indicators may be determined. The one or more first indicators may be determined based on the received first sensor data. The one or more first indicators may be likely to have affected the user 112 or the performance of the user 112 in the physical activity. In one or more embodiments, the circuitry 202 may be configured to determine the one or more first indicators which may be likely to have affected the user 112 or the performance of the user 112 in the physical activity. The one or more first indicators may be based on the received first sensor data. The details about the determination of the first indicators are provided, for example, in FIGS. 1 and 3A.

At 1210, the presentation data 116 may be generated. The presentation data 116 may be based on an application of the first ML model 104 on the determined one or more first indicators and the received first information 302B. The generated presentation data may include the one or more improvement suggestions for the user 112 in relation to the physical activity. In one or more embodiments, the circuitry 202 may be configured to generate the presentation data 116 based on the application of the first ML model 104 on the determined one or more first indicators and the received first information 302B. The generated presentation data 116 may include the one or more improvement suggestions for the user 112 in relation to the physical activity. The details about the generation of the presentation data 116 are provided, for example, in FIGS. 3A, 4A, 5A, and 7A.

At 1212, the display device 106 may be controlled to display the generated presentation data 116. In one or more embodiments, the circuitry 202 may be configured to control the display device 106 to display the presentation data 116 as described in FIGS. 3B, 4B, 5B, 5C, 7B, 8, 9A, 9B, 10, 11A, and 11B. Control may pass to end.

Various embodiments of the disclosure may provide a non-transitory computer readable medium and/or storage medium having stored thereon, instructions executable by a machine and/or a computer such as the electronic device 102. The instructions may cause the machine and/or computer to perform operations that may include reception of the first sensor data 302A associated with the movement pattern of the one or more parts of the body of the user 112. The first sensor data 302A may correspond to a duration in which the user 112 performs the physical activity. The operations may include reception of the first information 302B associated with the location where the user 112 performs the physical activity. The operations may further include determining the one or more first indicators which may be likely to have affected the user 112 or the performance of the user 112 in the physical activity. The one or more first indicators may be determined based on the received first sensor data 302A. The operations may further include generating the presentation data 116 based on application of the first ML model 104 on the determined one or more first indicators and the received first information 302B. The generated presentation data 116 includes the one or more improvement suggestions for the user 112 in relation to the physical activity. The operations may further include controlling the display device 106 to display the presentation data 116.

Exemplary aspects of the disclosure may include an electronic device (such as the electronic device 102 of FIG. 1) that may include circuitry (such as the circuitry 202). The circuitry may be configured to receive first sensor data (such as the first sensor data 302A) associated with a movement pattern of one or more parts of a body of a user (such as the user 112). The first sensor data 302A may correspond to a duration in which the user performs a physical activity. The circuitry 202 may further receive second sensor data (such as the second sensor data 408) that may include one or more biological markers of the body. The circuitry 202 may further receive first information 302B associated with a location where the user 112 performs the physical activity. The received first information 302B may include at least one of the location of the user, a ground elevation of the location, weather information associated with the location, and terrain information associated with the location.

In another embodiment, the circuitry 202 may be configured to receive second information associated with the performance of the user 112 in the physical activity. The circuitry 202 may further determine one or more first indicators which are likely to have affected the user 112 or the performance of the user 112 in the physical activity based on the received first sensor data 302A. The circuitry 202 may be further configured to generate presentation data (such as the presentation data 116) based on application of a first machine learning model (such as the first machine learning model 104) on the determined one or more first indicators, received second sensor data 408, the received first information 302B, and the received second information.

In an embodiment, the first sensor data 302A may include first accelerometer data associated with the movement pattern of an arm portion of the body. In such an embodiment, the circuitry 202 may be configured to generate motion detection data associated with the movement pattern of the arm portion based on the first sensor data 302A. The circuitry 202 may be configured to filter the generated motion detection data by removal of a first set of outlier samples from the generated motion detection data. The circuitry 202 may be further configured to determine the one or more first indicators by application of a motion classifier on the filtered motion detection data. The one or more improvement suggestions may be associated with a swing movement of the arm portion.

In an embodiment, the received first sensor data 302A may include second accelerometer data associated with the movement pattern of a foot portion of the body. In such an embodiment, the circuitry 202 may be configured to apply one or more signal processing operations on the second accelerometer data to determine the one or more first indicators including landing measurements associated with the foot portion and a running stride of the user 112. The one or more improvement suggestions in the determined one or more first indicators may be associated with the movement pattern of the foot portion.

In an embodiment, the circuitry 202 may receive breathing data (such as the breathing data 504) associated with the user 112. The breathing data 504 may correspond to the duration in which the user 112 performs the physical activity. The circuitry 202 may be further configured to process the received breathing data 504 to generate breath detection data. The circuitry 202 may further filter the generated breath detection data by removal of a second set of outlier samples from the generated breath detection data. The circuitry 202 may be further configured to determine the one or more second indicators including a breathing pattern of the user 112 based on the filtered breath detection data. The presentation data 116 may be generated based on application of the first ML model 104 on the determined one or more second indicators and the received second sensor data 408. The one or more improvement suggestions may be associated with the breathing pattern of the user 112.

In an embodiment, the circuitry 202 may be configured to control a set of image sensors to capture a set of images of the user 112. The set of images may be captured within the duration in which the user 112 performs the physical activity. The circuitry 202 may be further configured to determine skeletal joints of the user in at least one of the captured set of images. The circuitry 202 may be configured to apply a posture classifier on the determined skeletal joints to determine one or more third indicators comprising a first body posture of the user. Accordingly, the presentation data 116 may be generated based on further application of the first ML model 104 on the determined one or more third indicators. The one or more improvement suggestions may be associated with the first body posture.

In an embodiment, the circuitry 202 may be configured to apply a second machine learning model (such as the second machine learning model 210) on the determined one or more first indicators and the received first information 302B to generate a classification result. The circuitry 202 may be further configured to determine an experience level of user 112 in relation to the physical activity, based on the classification result. The determined experience level may be one of an amateur level athlete, an intermediate level athlete, or an expert level athlete. In such cases, the presentation data 116 may be generated further based on the determined experience level. In another embodiment, the generated presentation data 116 further includes visual data which compares of the one or more first indicators with known indicators of expert athletes.

In an embodiment, the circuitry 202 may be further configured to determine one or more injuries which are likely to be caused by the movement pattern or the performance of the physical activity. The one or more injuries may be determined based on analysis of the determined one or more first indicators. The presentation data 116 may further include information which informs the user about the one or more injuries and recommendations to avoid the one or more injuries.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system with information processing capability to perform a particular function either directly, or after either or both of the following: a) conversion to another language, code or notation; b) reproduction in a different material form.

While the present disclosure is described with reference to certain embodiments, it will be understood by those skilled in the art that various changes may be made, and equivalents may be substituted without departure from the scope of the present disclosure. In addition, many modifications may be made to adapt a particular situation or material to the teachings of the present disclosure without departure from its scope. Therefore, it is intended that the present disclosure is not limited to the particular embodiment disclosed, but that the present disclosure will include all embodiments that fall within the scope of the appended claims.

What is claimed is:

1. An electronic device, comprising: circuitry configured to:
receive a first sensor data associated with a movement pattern of one or more parts of a body of a user, wherein the first sensor data corresponds to a duration in which the user performs a physical activity;
receive a first information associated with a location where the user performs the physical activity, wherein the received first information comprises at least one of the location of the user, a ground elevation of the location, weather information associated with the location, and terrain information associated with the location;
determine, based on the received first sensor data, one or more first indicators which are likely to have affected the user or performance of the user in the physical activity;
generate presentation data based on application of a first machine learning model on the determined one or more first indicators and the received first information, wherein the generated presentation data comprises one or more improvement suggestions for the user in relation to the physical activity; and
control a display device to display the presentation data.

2. The electronic device according to claim 1, wherein the circuitry is further configured to receive second sensor data comprising one or more biological markers of the body, and
wherein the presentation data is generated based on further application of the first machine learning model on the received second sensor data.

3. The electronic device according to claim 1, wherein the circuitry is further configured to receive second information associated with the performance of the user in the physical activity, and
wherein the presentation data is generated based on further application of the first machine learning model on the received second information.

4. The electronic device according to claim 1, wherein the first sensor data comprises first accelerometer data associated with the movement pattern of an arm portion of the body.

5. The electronic device according to claim 4, wherein the circuitry is further configured to:
generate motion detection data associated with the movement pattern of the arm portion, based on the first sensor data;
filter the generated motion detection data by removal of a first set of outlier samples from the generated motion detection data; and
determine the one or more first indicators by application of a motion classifier on the filtered motion detection data.

6. The electronic device according to claim 5, wherein the one or more improvement suggestions are associated with a swing movement of the arm portion.

7. The electronic device according to claim 1, wherein the received first sensor data comprises second accelerometer data associated with the movement pattern of a foot portion of the body.

8. The electronic device according to claim 7, wherein the circuitry is configured to apply one or more signal processing operations on the second accelerometer data to determine the one or more first indicators comprising landing measurements associated with the foot portion and a running stride of the user, and
wherein the one or more improvement suggestions are associated with the movement pattern of the foot portion.

9. The electronic device according to claim 1, wherein the circuitry is further configured to:
receive breathing data associated with the user, wherein the breathing data corresponds to the duration in which the user performs the physical activity;
process the received breathing data to generate breath detection data;
filter the generated breath detection data by removal of a second set of outlier samples from the generated breath detection data; and
determine one or more second indicators comprising a breathing pattern of the user, based on the filtered breath detection data.

10. The electronic device according to claim 9, wherein the circuitry is further configured to receive second sensor data comprising one or more biological markers of the body, and
wherein the presentation data is generated based on further application of the first machine learning model on the determined one or more second indicators and the received second sensor data.

11. The electronic device according to claim 10, wherein the one or more improvement suggestions are associated with the breathing pattern of the user.

12. The electronic device according to claim 1, wherein the circuitry is configured to:
control a set of image sensors to capture a set of images of the user,
wherein the set of images is captured within the duration in which the user performs the physical activity;
determine skeletal joints of the user in at least one of the captured set of images; and
apply a posture classifier on the determined skeletal joints to determine one or more third indicators comprising a first body posture of the user.

13. The electronic device according to claim 12, wherein the presentation data is generated based on further application of the first machine learning model on the determined one or more third indicators, and
wherein the one or more improvement suggestions are associated with the first body posture.

14. The electronic device according to claim 1, wherein the circuitry is configured to:
apply a second machine learning model on the determined one or more first indicators and the received first information to generate a classification result; and
determine an experience level of the user in relation to the physical activity, based on the classification result, wherein
the determined experience level is one of an amateur level athlete, an intermediate level athlete, or an expert level athlete, and
the presentation data is generated further based on the determined experience level.

15. An electronic device, comprising: circuitry configured to:
receive a first sensor data associated with a movement pattern of one or more parts of a body of a user,
wherein the first sensor data corresponds to a duration in which the user performs a physical activity;
receive a first information associated with a location where the user performs the physical activity:
determine, based on the received first sensor data, one or more first indicators which are likely to have affected the user or performance of the user in the physical activity;
generate presentation data based on application of a first machine learning model on the determined one or more first indicators and the received first information,
wherein the generated presentation data comprises one or more improvement suggestions for the user in relation to the physical activity and further comprises visual data which compares the one or more first indicators with known indicators of expert athletes; and
control a display device to display the presentation data.

16. The electronic device according to claim 1, wherein the circuitry is configured to:
determine one or more injuries which are likely to be caused by the movement pattern or the performance of the physical activity,
wherein the one or more injuries are determined based on analysis of the determined one or more first indicators, and
the presentation data further comprises information which informs the user about the one or more injuries and recommendations to avoid the one or more injuries.

17. A method, comprising:
receiving a first sensor data associated with a movement pattern of body of a user or one or more parts of the body,
wherein the first sensor data corresponds to a duration in which the user performs a physical activity;
receiving a first information associated with a location where the user performs the physical activity, wherein the received first information comprises at least one of the location of the user, a ground elevation of the location, weather information associated with the location, and terrain information associated with the location;
determining, based on the received first sensor data, one or more first indicators which are likely to have affected the user or performance of the user in the physical activity;
generating presentation data based on application of a first machine learning model on the determined one or more first indicators and the received first information,
wherein the generated presentation data comprises one or more improvement suggestions for the user in relation to the physical activity; and
controlling a display device to display the presentation data.

18. A non-transitory computer-readable medium having stored thereon, computer-executable instructions that when executed by an electronic device, causes electronic device to execute operations, the operations comprising:
receiving a first sensor data associated with a movement pattern of body of a user or one or more parts of the body,
wherein the first sensor data corresponds to a duration in which the user performs a physical activity;
receiving a first information associated with a location where the user performs the physical activity, wherein the received first information comprises at least one of the location of the user, a ground elevation of the location, weather information associated with the location, and terrain information associated with the location;
determining, based on the received first sensor data, one or more first indicators which are likely to have affected the user or performance of the user in the physical activity;
generating presentation data based on application of a first machine learning model on the determined one or more first indicators and the received first information,
wherein the generated presentation data comprises one or more improvement suggestions for the user in relation to the physical activity; and
controlling a display device to display the presentation data.

* * * * *